US005747048A

United States Patent [19]
Kjeldsen et al.

[11] Patent Number: 5,747,048
[45] Date of Patent: May 5, 1998

[54] MONOCLONAL ANTIBODIES AND VACCINE DEVELOPMENT DIRECTED TO HUMAN CANCER-ASSOCIATED ANTIGENS BY IMMUNIZATION WITH ANIMAL AND HUMAN MUCIN AND WITH SYNTHETIC CARBOHYDRATE-CARRIER CONJUGATES

[75] Inventors: Thomas J. Kjeldsen; Henrik Clausen; Anil Singhal; Tatsushi Toyokuni; Helio Takahashi; Sen-itiroh Hakomori, all of Seattle, Wash.

[73] Assignee: The Biomembrane Institute, Seattle, Wash.

[21] Appl. No.: 354,157

[22] Filed: Dec. 6, 1994

Related U.S. Application Data

[60] Continuation of Ser. No. 931,339, Aug. 18, 1992, abandoned, which is a division of Ser. No. 807,817, Dec. 16, 1991, Pat. No. 5,229,289, which is a continuation of Ser. No. 317,492, Mar. 1, 1989, abandoned, which is a continuation-in-part of Ser. No. 167,786, Mar. 11, 1988, abandoned.

[51] Int. Cl.$^6$ .......................... A61K 38/14; A61K 39/00; A61K 39/39; C07K 14/82
[52] U.S. Cl. .................. 424/277.1; 424/184.1; 424/193.1; 514/8; 514/23; 530/395
[58] Field of Search .................. 530/350, 395; 424/184.1, 185.1, 277.1, 278.1; 514/2, 8, 23

[56] References Cited

U.S. PATENT DOCUMENTS 4,444,744   4/1984   Goldenberg ........................ 424/1.1

OTHER PUBLICATIONS

Kurosaka et al., JBC 263, 8724 (1988).
Kurosawa A., et al., FEBS Lett 215:137–139, 1987.
Hakomori et al., J. Biol. Chem. 258:11819–11822.
Ross et al., Journal of the National Cancer Institute, vol. 73, p. 731 (1984).
Nuti M, et al., Intl. J. Cancer 29:539–545, 1982.
Johnson VG, et al., Cancer Res. 46:850–857, 1986.
Thor A, et al., Cancer Res. 46:3118–3124, 1986.
Feizi, T., et al; Biochem. Soc. Trans. 12(4):591–6 (1984), "Mucin–type glycoproteins".
Hakomori, S., et al. Cancer Res. 45(6):2405–14 (1985) "Aberrant Glycosylation in Cancer Cell Membranes as Focused on Glycolipids: Overview and Perspectives".
Houghton, A.N. et al. PNAS USA 82:1242–46 (1985) "Mouse Monoclonal IgG3 Antibody Detecting GD3 Ganglioside: A Phase I Trial in Patients with Malignant Melanoma".
Schreiber, H. In Fundamental Immunology, W. F. Paul editor (1989). "Tumor Immunology" pp. 923–955.
Sundsmo, J.S. et al. Biochem. Biophys. Res. Comm. 68(3):799–806 (1976), "Lacto–N–Neotetrasylceramide (Paragloboside) as a Possible Tumor–Associated Surface Antigen . . . ".
Gupta, R. K. et al. Vaccine 11(3):293–306 (1993) "Adjuvants—a Balance Between Toxicity and Adjuvanicity".
Rabinovich, N. B. et al. Science 265:1401–4 (2 Sep. 1994), "Vaccine Technologies: View to the Future".
Dermer, G. B. Bio/Technology 12:320(Mar. 1994), "Another Anniverrsay of the War on Cancer".
Osband, M. E. et al., Immunol. Today 11(6):193–195 (1990), "Problems in the Investigational Study and Clinical Use of Cancer Immunotherapy".
Springer, Georg F., Science 224:1198–1206, "T and Tn, General Carcinoma Autoantigens", Jun. 1984.

Primary Examiner—Thomas M. Cunningham
Attorney, Agent, or Firm—Sughrue, Mion, Zinn, Macpeak & Seas, PLLC

[57] ABSTRACT

A method of producing monoclonal antibodies that bind to human cancer-associated mucin-type glycoprotein antigens comprising: (1) immunizing a host with a core structure of a mucin-type glycoprotein; (2) fusing splenocytes from said immunized host with myeloma cells to form hybridoma cells; (3) culturing said hybridoma cells on selective medium; (4) selecting hybridoma cells surviving step (3) that secrete antibody that binds to said core structure of a mucin-type glycoprotein; (5) cloning said selected hybridoma cells from step (4); (6) culturing said cloned hybridoma cells; and (7) recovering said antibody. Hybridomas and monoclonal antibodies produced by the above-described method. Methods of passive and active immunization employing the monoclonal antibodies and mucin-type glycoproteins or synthetic oligosaccharide-carrier conjugates.

9 Claims, 10 Drawing Sheets

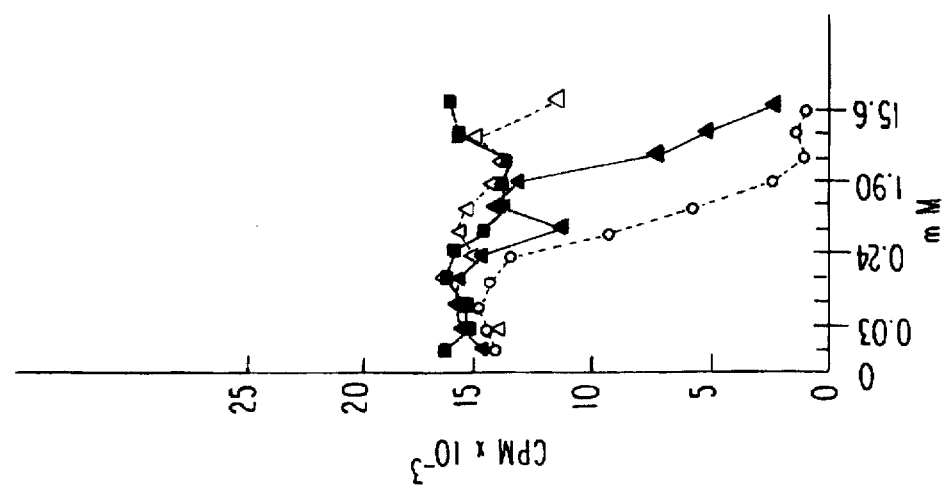
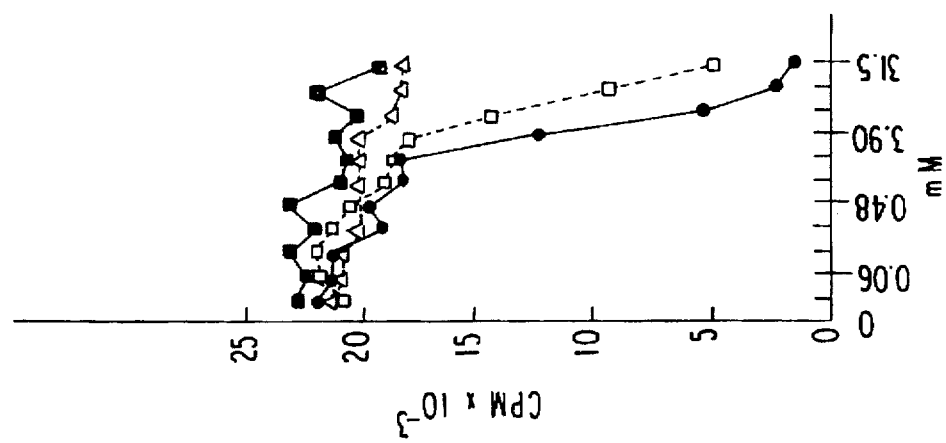
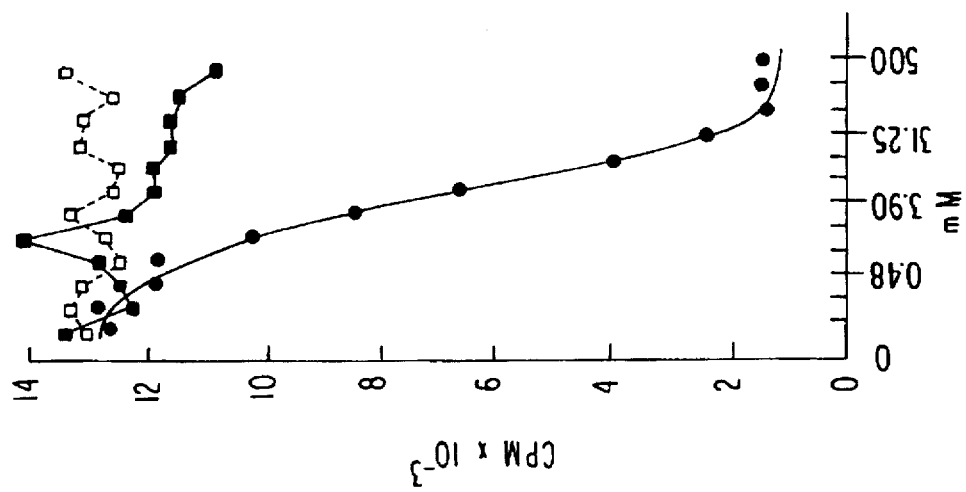

CELL BINDING ASSAY

FIG. 12A
SCHEME I
TRIVALENT CONJUGATE
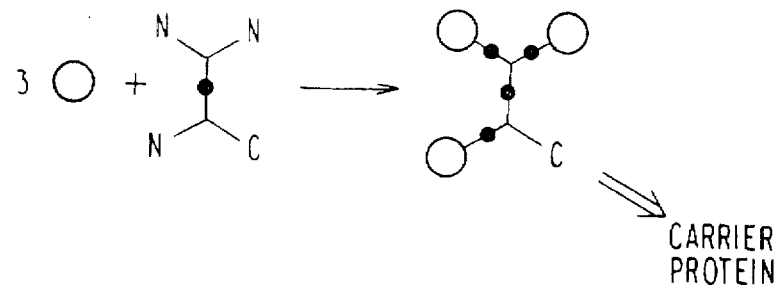
⇒ CARRIER PROTEIN
NONAVALENT CONJUGATE
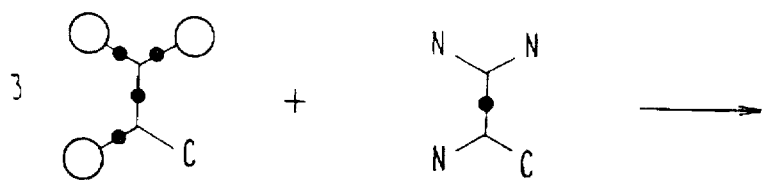
⇒ CARRIER PROTEIN
○ Tn-ANTIGEN
• AMIDE BOND
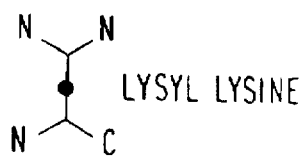 LYSYL LYSINE

FIG.12B
SCHEME II
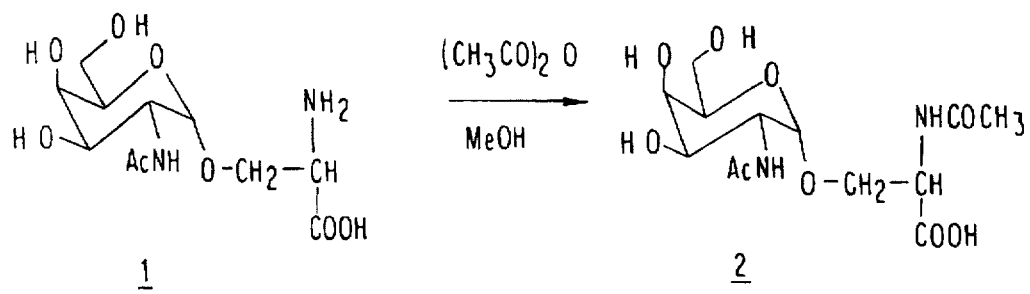
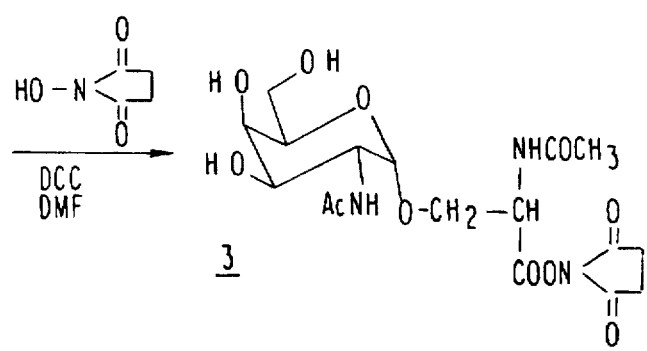
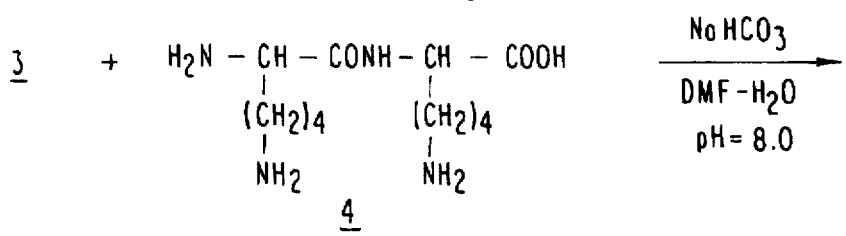
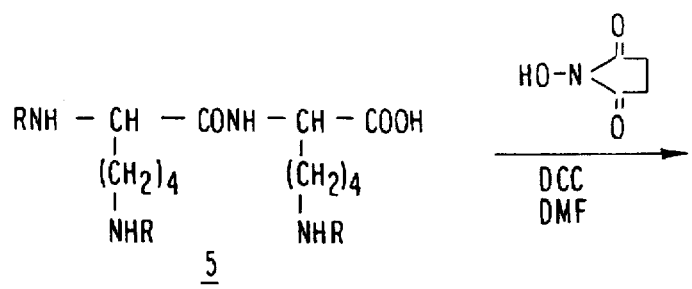
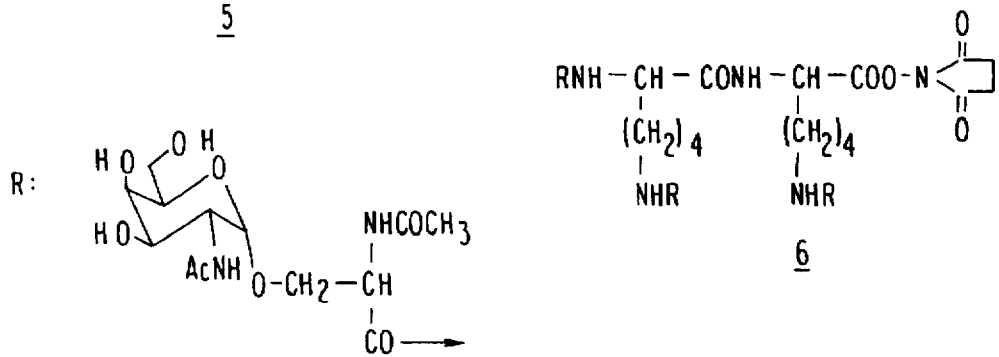

MONOCLONAL ANTIBODIES AND VACCINE DEVELOPMENT DIRECTED TO HUMAN CANCER-ASSOCIATED ANTIGENS BY IMMUNIZATION WITH ANIMAL AND HUMAN MUCIN AND WITH SYNTHETIC CARBOHYDRATE-CARRIER CONJUGATES

This is a continuation of U.S. application Ser. No. 07/931,339 filed 18 Aug. 1992, which is abandoned; a divisional of application Ser. No. 07/807,817 filed 16 Dec. 1991, now U.S. Pat. No. 5,229,289; which is a continuation of application Ser. No. 07/317,492 filed 1 Mar. 1989, abandoned; which is a continuation-in-part of application Ser. No. 07/167,786 filed 11 Mar. 1988, abandoned.

FIELD OF THE INVENTION

The present invention relates to new methods for the production of monoclonal antibodies specific to human cancer-associated antigens and to the hybridomas and monoclonal antibodies produced therefrom. More particularly, the present invention relates to new methods for the preparation of monoclonal antibodies directed to human cancer-associated antigens which use as the immunogen purified antigen whose structure is chemically defined and wherein the selection of the hybridoma cell lines producing the desired monoclonal antibody is made using mucin-type glycoprotein with a defined chemical structure. The procedure avoids a number of extra steps as compared to the current methods used for preparing monoclonal antibodies to human cancer-associated antigens. The present invention also relates to the hybridomas produced by the novel method and to the monoclonal antibodies secreted by the hybridomas. The qualities of the hybridomas have been proven to be as good as those of hybridomas prepared by conventional methods, and the monoclonal antibodies produced by the hybridomas are qualitatively as good as those produced by conventional methods, or even better in that the monoclonal antibodies of the present invention do not exhibit undesirable cross-reactivity.

The present invention also relates to methods of passive immunization of patients with cancer with those IgG monoclonal antibodies directed to mucin-type glycoproteins as well as to methods for vaccine development based on active immunization with the mucin-type glycoproteins or synthetic oligosaccharides linked to carrier macromolecules.

BACKGROUND OF THE INVENTION

A number of monoclonal antibodies after immunization with human tumor cells have been selected by positive reactivity with human cancer cell lines and negative reactivity with normal tissues and normal cell lines. Many of these antibodies have been identified as being directed to mucin-type glycoproteins, which are characterized by extremely heterogeneous disulfide inter-linked high molecular weight polypeptides having a large number of O-linked oligosaccharides. The majority of O-linked oligosaccharides consist of a disaccharide core (Galβ1→3GalNAcα1→O-Ser/Thr) to which a number of sugar residues such as sialic acid, fucose, and N-acetyl glucosamine are linked to form highly complex structures in the human species. These mucin-type glycoproteins are mainly present in epithelial cells and are secreted from goblet cells to form mucinous secretions.

Associated with oncogenic transformation, synthesis of many sugar chains is blocked (Hakomori S., Murakami W. T., *Proc. Natl. Acad. Sci. USA*, 59:254–261, 1968 and Hakomori S., *Cancer Res.*, 45:2405–2414, 1985). Synthesis of carbohydrate chains in mucin-type glycoproteins is also blocked strongly in many human cancers, thus forming a number of mucin-type glycoproteins with short carbohydrate chains and without peripheral structure, i.e., without modification of the core structure. Among those glycoproteins with incomplete oligosaccharide chains, T, Tn, and sialyl-Tn have been identified. These are the common core structures of all mucin-type glycoproteins present in normal tissues in a cryptic form (Springer G., *Science*, 224:1198–1206, 1984 and Hirohashi S. et al. *Proc. Natl. Acad. Sci. USA*, 82:7039–7043, 1985).

The current methods used to prepare monoclonal antibodies to human cancer-associated antigens use as the immunogen tumor tissue homogenate or tumor cell lines, and the hybridoma is selected by analyzing the specificity of the antibodies produced with a large number of tumor cells and tissue sections.

For example, the blood group A cross-reacting antigenicity of α-GalNac residue linked to a serine or threonine of a glycoprotein has been described by Uhlenbruck and associates as the Tn antigen detectable by various GalNac lectins (*Helix pomatia, Soia hispida*, and *Sarothamnus scoparius*) that preferentially agglutinate blood group A erythrocytes. The epitope represents the innermost α-GalNAc residue of O-linked carbohydrate chains present in transmembrane glycoproteins as well as mucin-type glycoproteins. Therefore, the antigen is cryptic in normal cells or secretions, but becomes exposed after desialylation followed by Smith degradation (Dahr, W., et al, *Vox Sang.*, 27:29–42, 1974). The Tn antigen has also been described by Springer and associates as the precursor of the Thomsen-Friedenreich antigen (T antigen), and both Tn and T antigens are expressed in breast cancer (Springer, G. F., et al, *J. Natl. Cancer Inst.*, 54:335, 1975) and various other cancers (Springer, G. F., et al *Cancer*, 55:561–569, 1985). However, the wide occurrence of the antigen in various types of human cancer and its restricted distribution in normal tissues were not well recognized until monoclonal antibodies specific to this epitope were recently established (Hirohashi, S. et al, *Proc. Natl. Acad. Sci. USA*, 82:7039–7043, 1985). The IgM antibodies NCC-LU-35 and NCC-LU-81 were originally established after immunization of mice with human lung squamous cell carcinoma Lu65 and selected by specific reactivity with tumors but not with normal tissues. These antibodies were shown to cross-react with A antigen and were identified as being directed to the Tn antigen (Hirohashi, S. et al, *Proc. Natl. Acad. Sci. USA*, 82:7039–7043, 1985). Although a great deal of cross-reactivity with blood group A antigen was demonstrated for NCC-LU-35 and to a lesser extent for NCC-LU-81, these antibodies are capable of defining Tn antigen specifically in tumors of blood group O and B individuals.

Since the reactivity of these anti-Tn antibodies was found to be highly restricted to non-A tumor tissues (Hirohashi, S. et al, *Proc. Natl. Acad. Sci. USA*, 82:7039–7043, 1985), it would be highly desirable to obtain the IgG version of the anti-Tn antibody without cross-reactivity to blood group A, since only IgG antibodies are capable of provoking antibody dependent cytotoxic effects on tumor cells (Young, W. W., Jr. and Hakamori, S., *Science*, 211:487–489, 1981; Houghton, A.N., et al, *Proc. Natl. Acad. Sci. USA*, 82:1242–1246, 1985; Herberman, R. B., et al, In: R. A. Reisfeld and S. Sell (eds.). *Monoclonal Antibodies and Cancer Therapy*, pp. 193–203, Alan R. Liss, Inc., New York, 1985; and Herlyn, D. M., et al, *Cancer Res.*, 40:717–721, 1980). IgG antibodies are also more suitable than IgM for preparation of conjugates with toxins, other antitumor reagents, and radioactive or paramagnetic markers for therapeutics as well as for imaging of tumors.

Further, two monoclonal antibodies, B72.3 (Nuti, M., et al, *J. Inst. Cancer*, 29:539–545, 1982; Thor, A., et al, *Cancer Res.*, 46:3118–3124, 1986; and Johnson, V. G., et al, *Cancer Res.*, 46:850–857, 1986) and MSL102 (Kurasawa, A. et al, In: Tumor marker and their significance in the management of breast cancer. (Eds. Dao, T., Brodie, A., and Ip, C.) p. 47–70, Alan R. Liss Inc., N.Y., 1986) have been established after immunization with human metastatic breast cancer and a colonic cancer cell line, respectively, that show highly specific reactivity with various human cancers and restricted reactivity with normal tissue.

However, these current methods require a large number of steps and, therefore, are quite cumbersome and time consuming.

Accordingly, a more efficient method for producing monoclonal antibodies to human cancer-associated antigens would be desirable as would the isolation of hybridomas that secrete monoclonal antibodies that do not exhibit undesirable cross-reativity with glycoproteins having normal carbohydrate sequence and structure.

Further, active immunization in order to suppress tumor growth has had a long history in tumor immunology. Some successful results have been obtained in experimental tumors, but many other attempts have failed. This was partially due to the fact that the tumor antigens used were not chemically well defined, and therefore, their ability to induce host immune response to suppress tumor growth was ambiguous. Recently, a number of tumor-associated carbohydrate antigens defined by monoclonal antibodies have been chemically well characterized. The use of such antigens as immunogens to suppress tumor growth is now possible.

Chemically defined cancer-associated glycoproteins themselves could be used to actively immunize cancer patients in order to elicit their endogenous immune response against tumors. A glycoprotein, TCA, isolated from Lewis lung carcinoma bearing T and Tn antigens was used to immunize cancer patients, which resulted in partial or complete regression of 33/71 cancer patients (Adachi, M., et al., *Anticancer Research* 4:1–4, 1984; Adachi, M., et al., *Anticancer Research*, submitted for publication).

SUMMARY OF THE INVENTION

Accordingly, it is an object of the present invention to provide novel methods for the preparation and establishment of monoclonal antibodies directed to human cancer-associated mucin-type glycoprotein antigens which methods avoid a number of extra steps required by the current method and which give hybridomas which have qualities as good as those prepared by conventional methods.

It is also an object of the present invention to provide hybridomas that secrete monoclonal antibodies to particular tumor-associated antigens.

It is a further object of the present invention to provide monoclonal antibodies which have qualities at least as good as those prepared by conventional methods or even better qualities in that the monoclonal antibodies do not exhibit undesirable cross-reactivity with glycoproteins having normal carbohydrate structure.

It is an even further object of the present invention to provide a method of vaccine development, i.e., of preventing growth and replication of cancer cells by administering animal or human glycoprotein, or synthetic oligosaccharide-carrier polymer complex that can induce antibodies or other immune responses specific for antigens expressed by the cancer cells.

Another object of the present invention is to provide a method of treating cancer which employs antibodies that are directed to the carbohydrates associated with the core structures of mucin-type glycoproteins and are specific for antigens expressed by the cancer cells.

These and other objects have been obtained by providing a method of producing monoclonal antibodies that bind to human cancer-associated mucin-type glycoprotein antigens comprising: (1) immunizing a host with a core structure of a mucin-type glycoprotein; (2) fusing splenocytes from the immunized hosts with myeloma cells to form hybridoma cells; (3) culturing the hybridoma cells on selective medium; (4) selecting hybridoma cells surviving step (3) that secrete antibody that binds to the core structure of a mucin-type glycoprotein; (5) cloning the selected hybridoma cells from step (4); (6) culturing the cloned hybridoma cells; and (7) recovering the antibody.

The present invention also provides a hybridoma that secretes a monoclonal antibody having the following identifying characteristics:

(1) $IgG_{2a}$ isotype, (2) Reacts with Tn antigen, (3) Specific to N-acetylgalactosamine (GalNAc), but not to N-acetylglucosamine (GlcNAc), galactose (Gal) or glucose (Glc), and (4) Epitopic specificity to $\alpha$-N-acetylgalactosamine ($\alpha$-GalNAc) and not $\beta$-N-acetylgalactosamine;

(5) Does not cross-react with blood group A;

A hybridoma that secretes a monoclonal antibody having the following identifying characteristics:

(1) IgM isotype, (2) Reacts with sialyl-Tn antigen and not with T or Tn antigen, and (3) Epitopic specificity to NeuAc$\alpha$2→6GalNAc$\alpha$1→O-Ser/Thr and not to NeuAc$\alpha$2-6GalNAc$\beta$1→O-Ser/Thr; and A hybridoma that secretes a monoclonal antibody having the following identifying characteristics:

(1) $IgG_1$ isotype, (2) Reacts with sialyl-Tn antigen and not with T or Tn antigen, (3) Epitopic specificity to NeuAc$\alpha$2→6GalNAc$\alpha$1→O-Ser/Thr and not to NeuAc$\alpha$2→6GalNAc$\beta$1→O-Ser/Thr, and (4) Can readily be converted to Fab or $(Fab)_2$ fragments.

In a further embodiment, the present invention provides the monoclonal antibodies secreted by the above-identified hybridomas. The antibodies are especially useful for passive immunization of patients with cancer expressing core structures of mucin-type glycoproteins, i.e., Tn and sialyl-Tn structures.

In an ever further embodiment, the present invention provides a method of preventing growth and replication of cancer cells that express the core structure of a mucin-type glycoprotein comprising inducing an anti-cancer cell immune response by administering to a subject a vaccine comprising:

(a) a pharmaecutically effective amount of an antigen comprising a purified mucin-type glycoprotein carrying a Tn or sialyl-Tn epitope, a purified core structure of a mucin-type glycoprotein or a chemically synthesized carbohydrate component linked to a carrier molecule and which are capable of inducing an immune response against the mucin-type glycoprotein, and (b) a pharmaceutically acceptable carrier, diluent or excipient.

The present invention also describes the use of a purified chemically-defined glycoprotein, i.e., bovine or ovine submaxillary mucin (BMS, OSM), carrying Tn and sialyl-Tn epitope, as an immunogen to prevent the growth of mouse tumor TA3HA in syngeneic mice and to increase survival of mice after challenge with tumor. Since the Tn and sialyl-Tn determinants are highly expressed in a large variety of human cancers (Hirohashi S., et al (1985) Proc Natl Acad Sci USA 82:7039–7043; Takahashi H K, et al (1988) Cancer Res 48:4361–4367; Kjeldsen T, et al (1988) Cancer Res 48:2214–2220; Kurosaka A, et al (1988) J Biol Chem 263:8724–8726), active immunization with BSM, OSM, or any other mucin-type glycoprotein having these determinants is expected to be useful to provide a vaccine for prevention of growth of human cancers. This provides a preferred embodiment of the vaccine.

The present invention also provides a method of treating cancer wherein the cancer cells express a core structure of a mucin-type glycoprotein comprising administering to a subject a medicament comprising:

(a) a pharmaceutically effective amount of an anti-cancer antibody produced against a purified core structure of a mucin-type glycoprotein, and (b) a pharmaceutically acceptable carrier, diluent or excipient.

Panel A: gel filtration pattern on Sepharose CL-4B of the total glycoprotein in the supernatant of LU-65 cells and the Tn activity assayed as described in Example 1. The ordinate indicates the binding of anti-Tn antibody NCC-LU-81, and the abscissa indicates the fraction number. The fractions indicated by the solid bar (fractions 7–15) were further purified on Sephacryl S200 (see below).

Panel B: gel filtration pattern on Sephacryl S200 of Tn activity in fractions 7–15 shown in Panel A. The left ordinate indicates UV absorption at 280 nm, and the right ordinate indicates Tn antibody binding activity. The abscissa indicates the fraction number and total volume of eluant. Open circles represent Tn antibody activity; closed circles represent protein concentration indicated by absorption at 280 nm.

FIGS. 2A–2C are graphs showing the results of assays to determine the inhibition of BM-8 antibody binding on solid phase Tn antigen by monosaccharide and by glycosides. The ordinates indicate antibody binding activity and the abscissas indicate sugar concentration in mM.

Panel A: inhibition of the antibody binding by monosaccharides. Closed squares represent GlcNAc or Glc inhibition for BM-8 binding; closed circles represent GalNAc inhibition for BM-8 binding; open squares represent Gal inhibition for BM-8 binding.

Panel B: inhibition of BM-8 antibody binding to solid phase Tn antigen by p-nitrophenyl α- and β-GalNAc. Closed circles repesent inhibition by p-nitrophenyl α-GalNAc; open triangles represent p-nitrophneyl-β-GalNAc; open squares represent GalNAc (mixture of α and β); closed squares represent GlcNAc.

Panel C: inhibition of LU-81 antibody binding to solid phase Tn antigen by p-nitrophenyl α and β-GlcNAc. Open circles represent p-nitrophenyl α-GalNAc; closed triangles represent GalNAc (mixture of α and β); open triangles represent p-nitrophenyl-β-GalNAc; closed squares represent GlcNAc.

Figure 3:
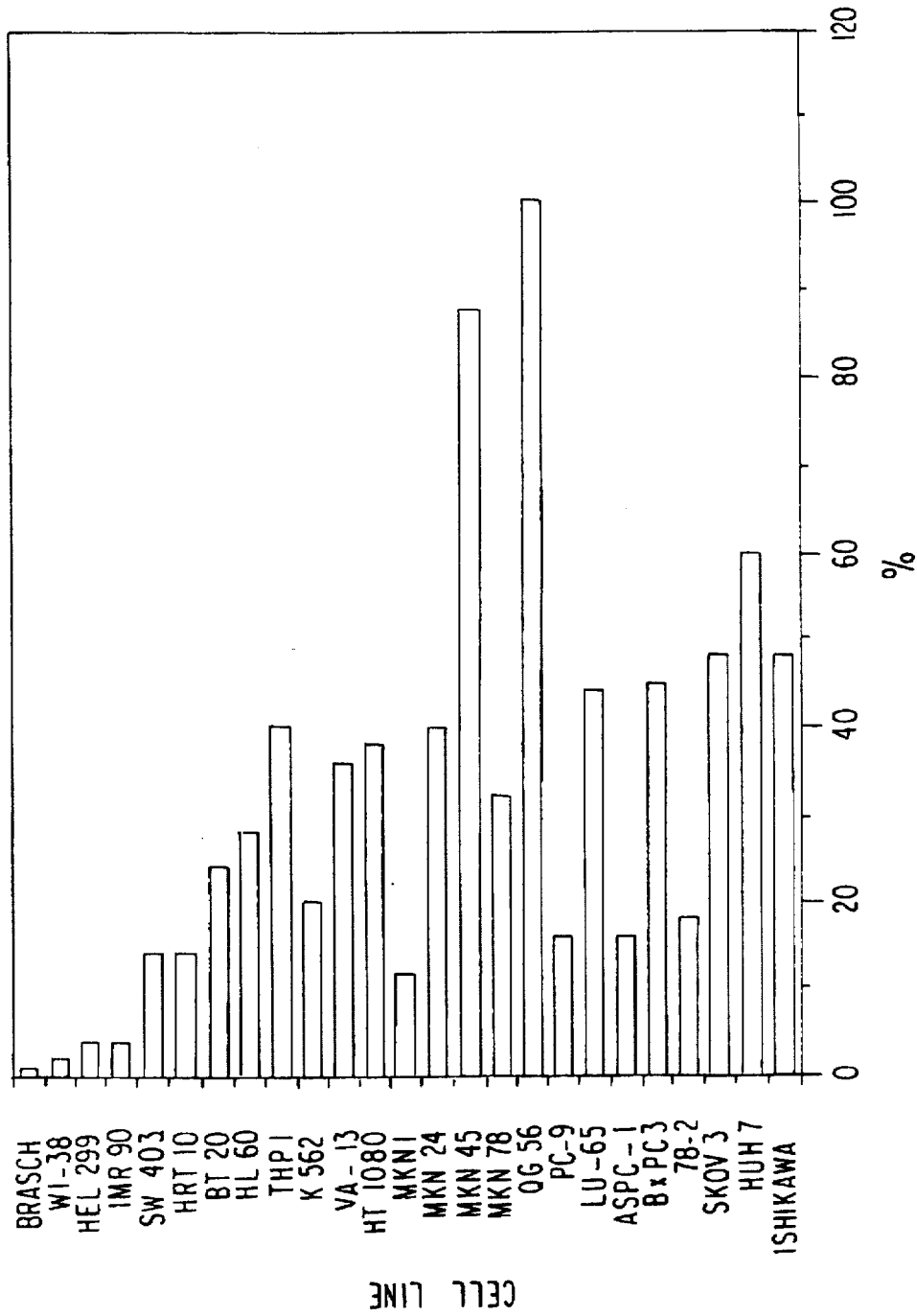

FIG. 3 is a graph showing the ability of BM-8 antibody to bind to various cell lines. Cell lines are indicated by each bar. Antibody binding is expressed as percent activity of QG-56 (100 percent).

Figure 4:
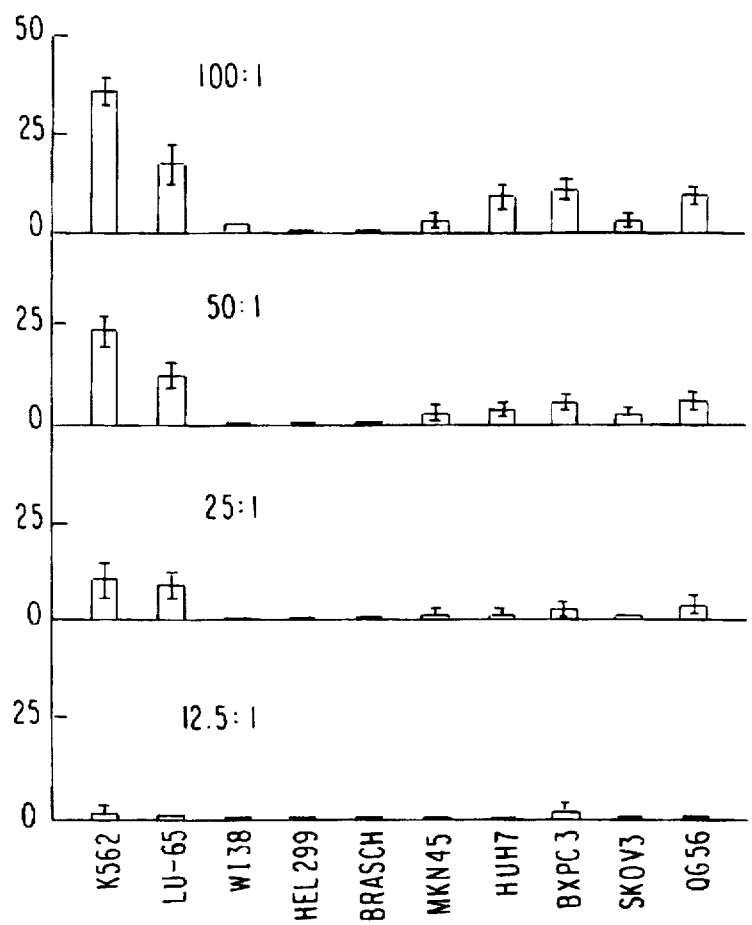

FIG. 4 is a graph showing the antibody-dependent cytotoxicity of various cell lines induced by BM-8 antibody. Four panels indicate the tumor cell lysis occurring at different effector to target cell ratios.

Figure 5A:
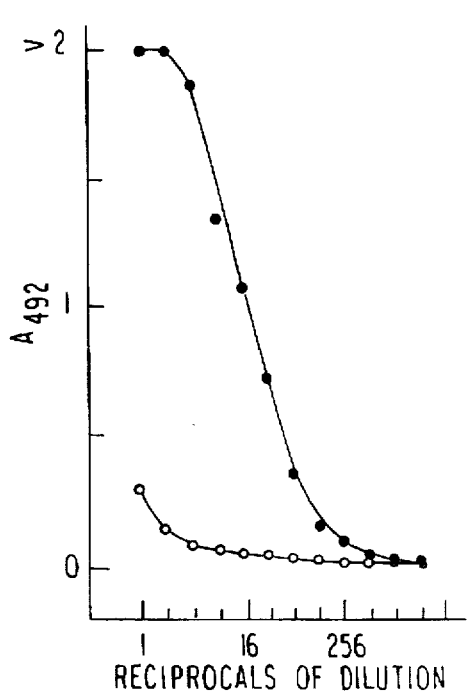
Figure 5B:
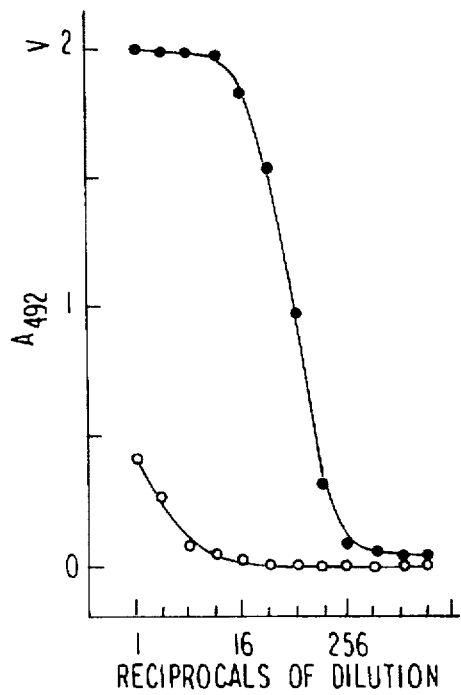

FIGS. 5A and 5B are two graphs showing the reactivity of monoclonal antibody BM-3 to solid phase OSM.

Panel A: Reactivity of BM-3 with OSM at various concentrations of BM-3 supernatant.

Panel B: Reactivity of BM-3 with various concentrations of OSM.

Reactivity with native OSM is indicated by closed circles and reactivity with neuraminidase treated OSM is indicated by open circles.

Figure 6A:
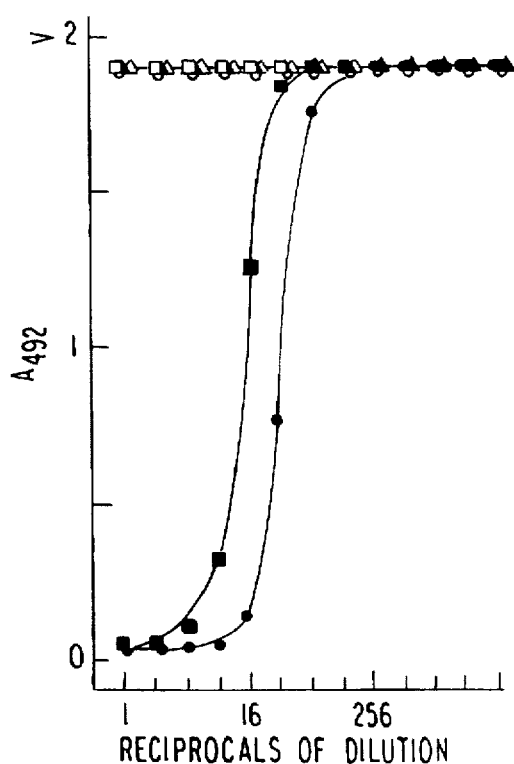
Figure 6B:
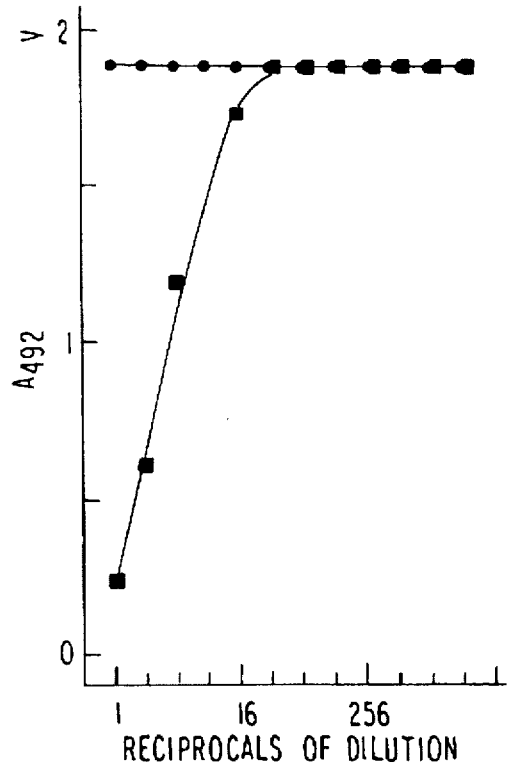
Figure 7A:
Figure 7B:
Figure 7C:
Figure 7D:

FIGS. 6A and 6B are two graphs showing the inhibition of BM-3 reactivity with OSM with different saccharides.

Panel A: inhibition of BM-3 with the monosaccharides fucose (open circles), galactose (open squares), glucose (closed triangles), N-acetylglucosamine (open triangles), N-acetylgalactosamine (closed squares), and N-acetylneuraminic acid (closed circles).

Panel B: inhibition of BM-3 with the disaccharides NeuAcα2→6GalNAcα1→serine (closed squares) and lactose (closed circles).

FIGS. 7A–7D show immunoperoxidase staining of formalin-fixed paraffin-embedded malignant tumors using BM-3 monoclonal antibody.

Panel A: BM-3 reactivity with a lung adenocarcinoma whereas normal lung are not stained (X90).

Panel B: staining of moderately differentiated colon adenocarcinoma, surrounding normal cells and stroma are nonreactive.

Panel C: Mucinous stomach carcinoma showing heterologous BM-3 staining of cancer cells (X90).

Panel D: BM-3 staining of acinar lung adenocarcinoma, normal lung tissue are not stained.

Figure 8A:
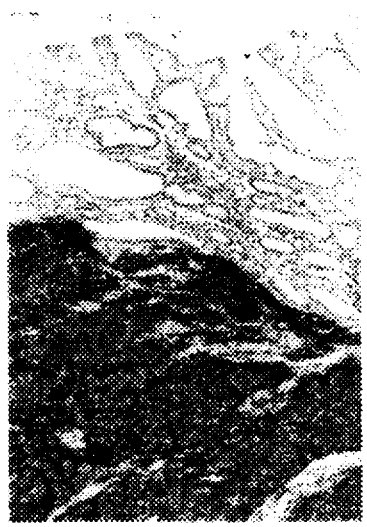
Figure 8B:
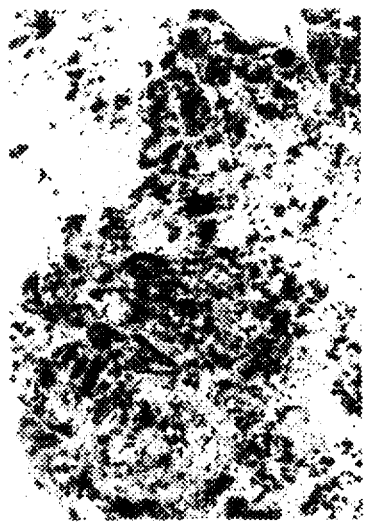
Figure 8C:
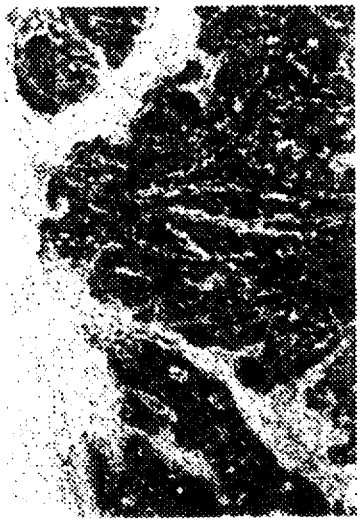

FIGS. 8A and 8C show immunoperoxidase staining of formalin-fixed paraffin-embedded malignant tumors using BM-4 monoclonal antibody.

Panel A: BM-4 reactivity with a lung adenocarcinoma (X40).

Panel B: BM-4 staining of a mucinous stomach carcinoma (X90).

Panel C: BM-4 reactivity with a moderately differentiated colon adenocarcinoma, normal colon cells and stroma are unreactive (X90).

Figure 9:
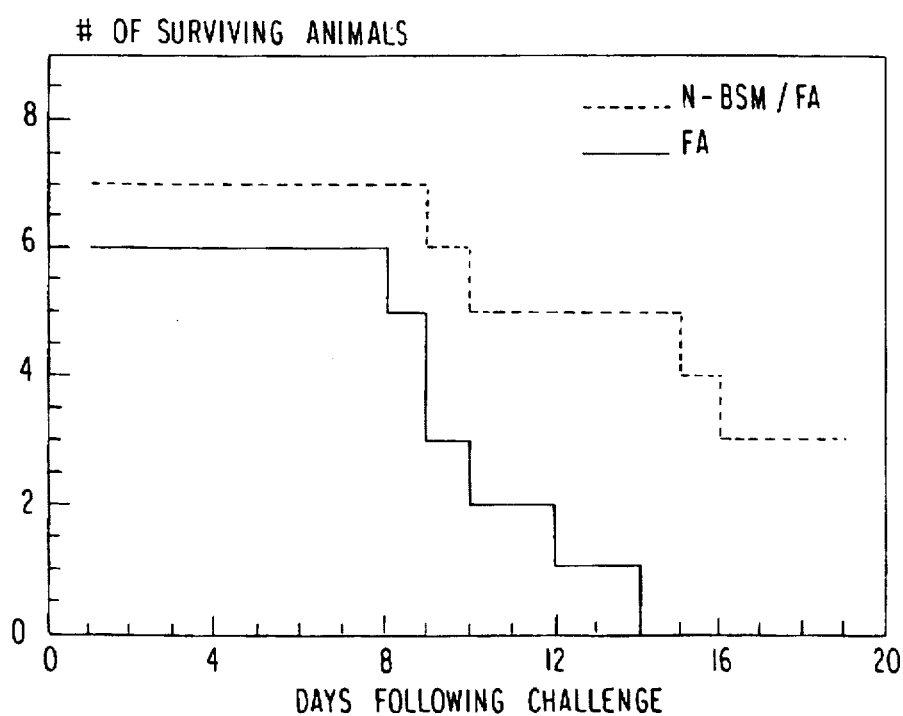

FIG. 9 shows the effect of neuraminidasetreated BSM (N-BSM) on survival of mice challenged with liver TA3HA cells. Solid line represents mice immunized with Freund's adjuvant (FA) alone; dashed line represents mice immunized with N-BSM.

Figure 10:
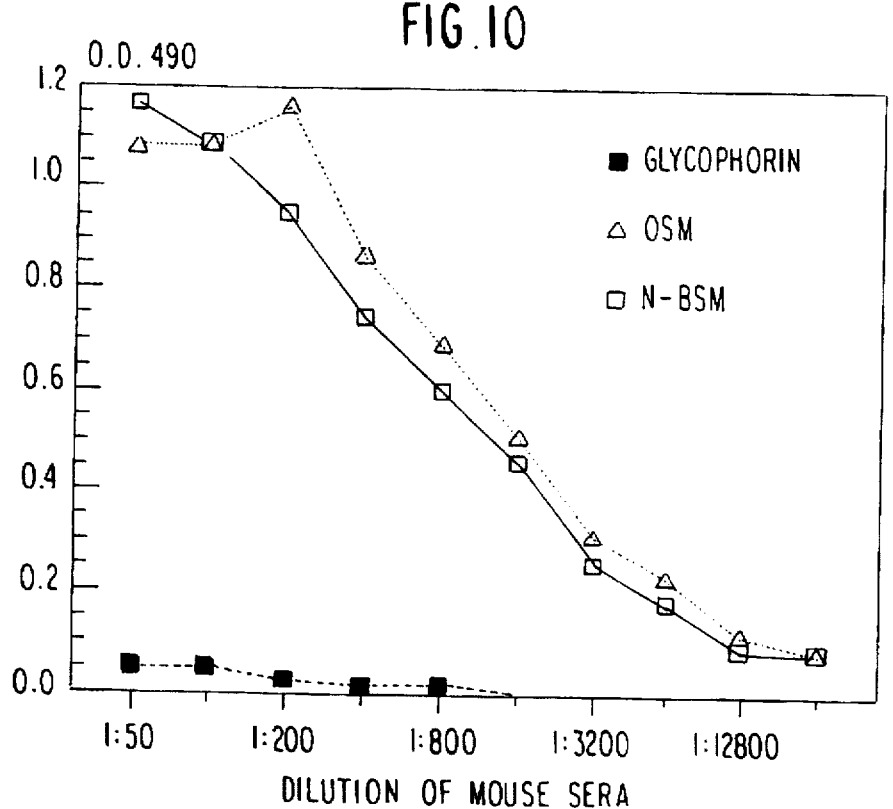

FIG. 10 shows the effect of N-BSM immunization of anti-Tn, anti-sialyl-Tn, or anti-T antibody titers in mouse sera. Open squares represent antibody titers against N-BSM (Tn); open triangles represent antibody titers against OSM (sialyl-Tn); closed squares represent antibody titers against neuraminidase-treated glycophorin A (T).

Figure 11:
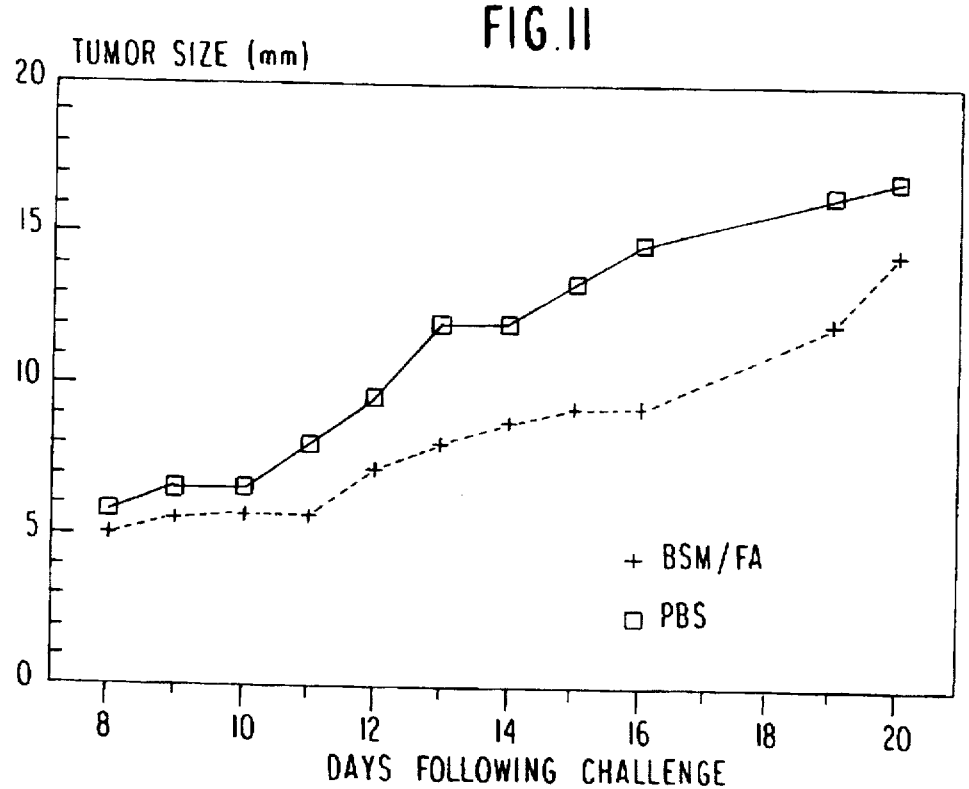

FIG. 11 shows the effect of N-BSM immunization on tumor size. Open squares indicate the mice immunized with FA; plus signs indicate mice immunized with N-BSM in Freund's adjuvant.

FIGS. 12A and 12B are schematic representations of the chemical synthesis of the carbohydrate epitope Tn as described in Example 4. Synthesis of sialyl-Tn could readily be achieved by adding a sialyl residue enzymatically or chemically.

DETAILED DESCRIPTION OF THE INVENTION

For the purposes of the present invention, the following terms have the meanings set forth below.

Mucin-Type Glycoprotein—A high molecular weight protein (Mr>$10^6$) with a high degree of O-linked glycosylation at serine or threonine residues. Mucin-type glycoproteins are further polymerized by S-S-dependent linkage and are the major components of epithelial secretions.

Core Structure Of Mucin-Type Glycoprotein—Basic carbohydrate structure without peripheral substitution and which is directly linked to the protein moiety of a mucin glycoprotein. The most frequent and the major such structure is the same as T antigen (see below). All the following core structures—T, Tn, and sialyl Tn—are common in all types of mucin glycoproteins irrespective of species (various animals and man).

T-Antigen—A disaccharide consisting of one mole each of Gal and GalNAc with a structure as follows: Galβ1→3GalNAc. The reducing terminal GalNAc is α-linked to the hydroxyl group of a serine or threonine residue of a polypeptide chain.

Tn Antigen—An antigen wherein the innermost α-GalNAc residue is directly linked to the hydroxyl group of a serine or threonine residue of a polypeptide chain. Since α-GalNAc is a part of blood group A antigen, many anti-Tn antibodies cross-react with A antigen.

Sialyl-Tn Antigen—An antigen wherein the sixth hydroxyl group of the α-GalNAc residue of the Tn antigen is substituted with sialic acid, i.e., NeuAcα2→6GalNAc α-linked to the hydroxyl group of a serine or threonine residue of a polypeptide chain.

The structures of the T antigen, Tn antigen and sialyl-Tn antigen are shown in the table below.

| Antigen | Structure |
| --- | --- |
| Tn | GalNAcα1->O-Ser or Thr |
| sialyl-Tn | NeuAcα2->6GalNAcα1->O-Ser or Thr |
| T | Galβ1->3GalNAcα1->O-Ser or Thr |

According to the present invention, there are provided novel methods for producing monoclonal antibodies directed to human cancer-associated mucin-type glycoprotein antigens. Two important aspects of the novel methods are: (1) that the immunogen used in the method is a purified or synthetic antigen whose structure is chemically well defined, and (2) that the selection of the hybridoma is made by using the same immunogen having a chemically defined structure.

Immunogen Preparation

According to the present invention, the immunogen used to obtain the antibody is a core structure of a mucin-type glycoprotein, as defined above. Specifically, any core structure of a mucin-type glycoprotein can be used as long as the glycoprotein has a sufficiently high molecular weight to provide immunogenicity and is glycosylated to the same degree as mucin, i.e., more than 50% of total weight is glycosylated.

Examples of core structures of mucin-type glycoproteins which are useful as immunogens in the present invention include the T antigen, the Tn antigen, and the sialyl-Tn antigen, and animal mucins containing these antigens. Other core structures, such as Galβ1→3[GlcNAcβ1→4]GalNAc, GlcNAcβ1→4GalNAc, and Galβ1→3[Galβ1→4GlcNAcβ1→4]GalNAc, may also be used.

Especially preferred immunogens are the T antigen, the Tn antigen, and the sialyl-Tn antigen and animal mucins containing these antigens.

The immunogens can be obtained by enzymatic or chemical modification of a mucin-type glycoprotein to expose a core structure or by isolation of mucins having on them core structures. These mucins are present in some animal species.

Examples of types of enzymatic modifications that can be used to expose the core structure of various mucin-type glycoproteins include the elimination of the terminally located α2→3 sialyl residue by influenza virus sialidase or the total elimination of all sialic acid residues by *Clostridium perfringense* sialidase. Enzymatic modification can also include treatment with β-galactosidase (preferably from *Charonia lampas*), α-fucosidase, and N-acetylhexasaminidase. Enzymatic hydrolysis of mucin glycoprotein is described by Hirohashi et al. (*Proc. Nat. Acad. Sci. USA*, 82:7039–7043, 1985).

Examples of chemical reactions which can be used to expose the core structure of mucin-type glycoproteins include periodate oxidation followed by reduction with sodium borohydride and treatment with weak acid. The procedure is called Smith degradation (Spiro, G., *Methods Enzymol.*, 28:3–43, 1972). This chemical treatment eliminates non-reducing terminals of carbohydrate residues except sialic acid, which can be eliminated by sialidase treatment, as described above.

Examples of mucins isolated from animals that can be used as immungens include ovine submaxillary mucin (OSM) in which 90% of the carbohydrate chains consist of the sialyl-Tn antigen and bovine submaxillary mucin (BSM) in which 50% of the carbohydrate chains consist of the sialyl-Tn antigen and 30% of the carbohydrate chains consist of Tn antigen and other unidentified residues. Not all the structures of the mucin glycoproteins of animal species have been elucidated; however, novel structures such as the trihexosamine core (GlcNAcβ1→4[GlcNAcβ1→3] GalNAc), which was previously found in sheep gastric mucin (Hounsell, E. et al., *Biochem. Biophys. Res. Commun.*, 92:1143–1159, 1979) may well be present in some of the core structures of human cancer mucin and, if so, these can be used in the present invention. Systematic knowledge of mucin core structures of various animals species is incomplete, however, as the mucin core structures become known, one skilled in the art will readily be able to determine if they are useful in the present invention.

Additionally, on further systematic application with various animal species, common structures as immunogens might be found. Methods to elucidate such structures include alkaline hydrolysis in the presence of borohydride (β-elimination), methylation analysis, and mass spectrometry of each oligosaccharide liberated. These methods are compiled in a chapter recently published (Hakomori, S., and Kannagi, R. 1986. In Handbook of Experimental Immunology, Vol. I, Blackwell Scientific Publications, Oxford, pp. 9.1–9.39).

The immunogens are isolated and purified according to conventional methods.

For example, mucin-type glycoproteins which will be enzymatically or chemically modified to produce core structures can be isolated by gel filtration through Sepharose 4B or Sephacryl 200S.

The isolated glycoprotein is then enzymatically or chemically modified, by methods described above, to expose the core structure, and the core structure is purified for use as immunogen as follows: The modified mucin can be separated by gel filtration through Sepharose 4B or Sephacryl 200. High pressure chromatography on a synthetic molecular filter column (fast liquid chromatography; Pharmacia) is also useful to separate enzymatically or chemically modified mucins. However, as immunogen, the modified mucin does not need to be purified. The presence of a small quantity of unmodified mucin will not be harmful to use as an immunogen according to the present invention. Further, modification is usually quantitative, if proper precautions are taken.

Mucins which are derived from animal species and contain glycoproteins already in the form of a core structure are obtained by conventional methods. For example by gel filtration through Sepharose 4B, Sephacryl 200, or FPLC, as described above.

The thus derived animal mucins can be further purified for use as immunogens by the same methods, such as conventional gel filtration or FPLC as described above. However, the purity of the immunogen is not essential.

As mentioned above, especially preferred antigens are the T antigen, the Tn antigen and the sialyl-Tn antigen.

T antigen can be prepared by sialidase treatment (Hirohashi et al., Proc. Natl. Acad. Sci. USA, 82:7039–7043, 1985) of various glycoproteins which have oligosaccharides with the core structure shown below:

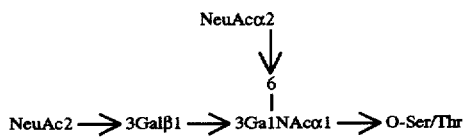

Typical examples of such glycoproteins are bovine submaxillary mucin and human erythrocyte glycophorin. Bovine submaxillary mucin can be obtained from bovine submaxillary glands by the procedure described by Nisizawa, K. and Pigman, W. (Arch. Oral Biol., 1:161, 1959). Ovine submaxillary mucin can be prepared by a similar method described previously (Tettamanti, G., and Pigman, W., Arch. Biochem. Biophys., 124:45–50, 1968).

Human erythrocyte glycophorine can be obtained from human erythrocyte membranes by the method originally described by Marchesi, V. T. and Andrews, E. D. (Science, 174:1247–1248, 1971).

Bovine submaxillary mucine and human erythrocyte glycoprotein are characterized by their strong reactivity with peanut lectin. However, any other type of glycoprotein having the above structure can be used for the purpose of obtaining T antigen.

Whether a glycoprotein has the above structure can be determined by affinity chromatography with a peanut lectin column (Carter, W. G., and Sharon, N., Arch. Biochem. Biophys., 180:570–582, 1977) or by immunoblotting of glycoproteins with anti-T antibody (available from ChemBiomed, Edmonston, Alberta, Canada).

The native form of ovine submaxillary mucin contains T antigen core without sialidase treatment; therefore it can be used as T antigen immunogen without further modification.

The native form of ovine submaxillary mucine is obtained from ovine submaxillary gland without further purification, but directly extracted and purified by the method previously described (Tettamanti and Pigman, Supra).

Tn antigen can be prepared from any type of glycoprotein by successive treatment with exoglycosidases and β-galactosidase; however, the β-galactosidase must be able to cleave the β1→3galactosyl structure linked to α-GalNAc.

Examples of suitable exoglycosidases and β-galactosidases include sialidase from Clostridium perfringense (Sigma Chemical Co., St. Louis, Mo.) and β-galactosidase of Charonia lampas (Seikagaku Kogyo, Tokyo, Japan) (Hirohashi et al., Supra).

The successive treatment with exoglycosidase and β-galactosidase is carried out as follows. A stable solution of mucin in suitable buffer containing 0.02% of a suitable detergent is mixed with enzyme and incubated at 37° C. for several to 18 hours. 50 mM of acetate buffer, pH 4.5–5.0, containing 0.02–0.05% Triton X-100 or NP40 is often used.

The thus treated glycoprotein is then purified for use as an immunogen by gel filtration with an appropriate column as described previously. The purification of immunogen is not essential, since the presence of unmodified mucin does not interfere with immune response to the modified mucin in vivo.

In addition, some animal mucins, such as ovine submaxillary mucin, contain a large quantity of Tn antigen in its native form. Therefore, native ovine submaxillary mucin is an excellent immunogen to elicit a Tn immune response.

Ovine submaxillary mucine can be obtained as described above.

Figure 1A:
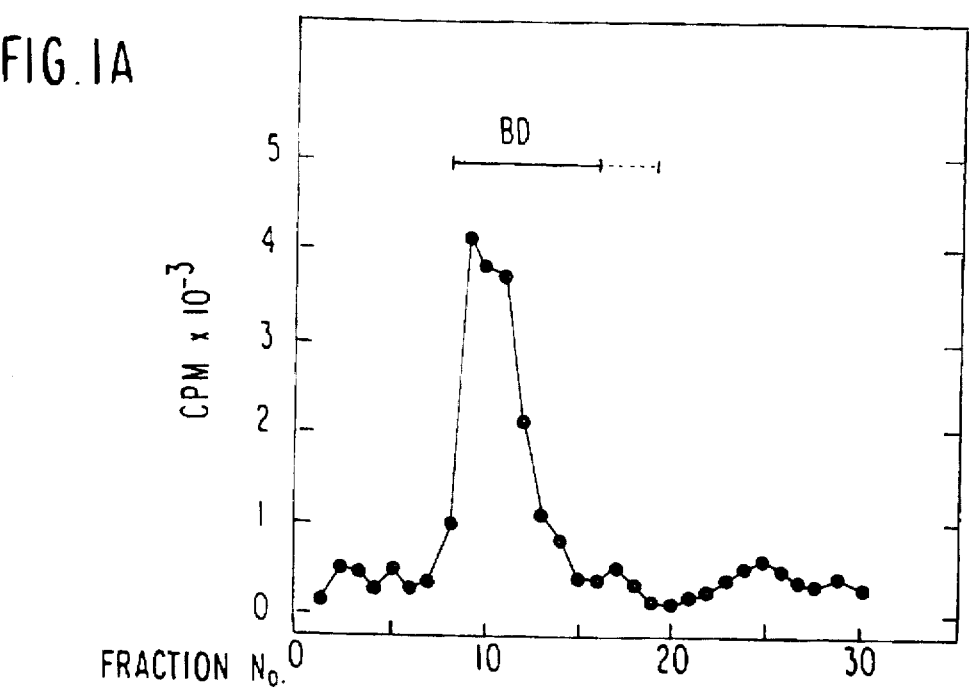
FIGS. 1A and 1B show gel filtration patterns showing Tn activity of glycoprotein present in the culture supernatant of human squamous cell carcinoma LU-65.
Figure 1B:
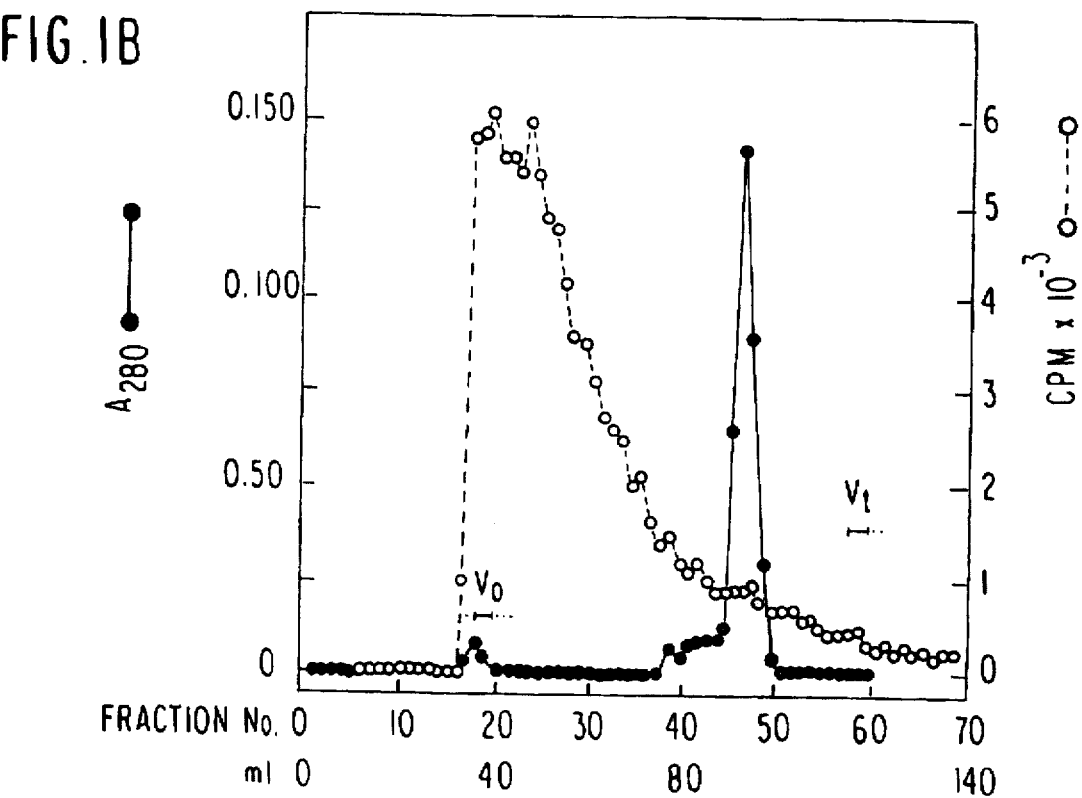

Another efficient Tn immunogen is a native Tn glycoprotein secreted from human squamous cell carcinoma cell line LU-65. The cells are cultured in suspension, and the spent culture medium is lyophilized to reduce its volume to 1/50 of the original volume. The concentrated spent medium is then dialyzed extensively against phosphate-buffered saline containing 0.01% sodium azide at 4° C. The dialyzed material is then placed on Sepharose 4B and gel filtrated. The void volume is pooled, concentrated further, and re-chromatographed on Sephacryl 200 (see FIG. 1). The glycoprotein fraction in the void volume is used as immunogen. Spent culture medium of those cell lines showing high reactivity with anti-Tn antibody, such as human squamous lung carcinoma cell line QG 56 and human hepatoma cell lines HUH-7 (see FIG. 5) can also be used for preparation of Tn antigen.

The distribution of the sialyl-Tn antigen is rather limited. However, one source of the sialyl-Tn antigen which is useful in the present invention is culture supernatants of squamous lung carcinoma cell lines QG 56 and LU-65 (Hirohashi S, et al, Proc. Natl. Acad. Sci. USA, 82:7039–7043, 1985).

A second source is again ovine submaxillary mucin, which contains a high density of sialyl-Tn.

In order to obtain sialyl-Tn antigen in a form useful as the immunogen for the present invention from culture supernatant, the various cell lines described above are cultured according to known methods The culture supernatants are treated to obtain sialyl-Tn antigen by the same procedure as described above for Tn antigen. However, all procedures must be completed within a limited time and at low temperature (4° C.), since the sialyl linkage is unstable.

A typical example of preparation of a mucin from culture supernatant is described in Example 1 below.

Ovine submaxillary mucin is obtained from ovine submaxillary gland and purified by the method of Tettamanti and Pigman (supra).

The carbohydrate epitopes T, Tn, and sialyl-Tn, can be chemically synthesized as shown in FIGS. 12A and 12B and covalently linked to synthetic or natural carriers such as polylysine, human serum albumen or highly branched synthetic carrier molecules based on the T-butoxycarbonyl β-alanine unit such as described by Tam (Proc. Natl. Acad. Sci. USA 85:5409–5413, 1988). A detailed description of the chemical synthesis of the carbohydrate epitope Tn is set forth in Example 4. Synthesis of sialyl-Tn can be readily achieved by adding a sialyl residue enzymatically or chemically.

Method of Immunization

The immunogens, prepared as described above, are treated for immunization as follows.

The glycoprotein antigen (e.g. 4.0 mg) is dissolved in distilled water (e.g. 4 ml), thoroughly mixed with an appropriate amount of acid-treated *Salmonella minnesota* (e.g. 16 mg), and lyophilized. The dried mixture is suspended in a suitable volume (e.g. 4.0 ml) of an appropriate carrier (e.g. 140 mM NaCl containing 20 mM phosphate buffer, pH 7.0), and aliquots of about 100 µl (i.e., 100 µg of mucin and 400 µg of bacteria) are injected intravenously.

The immunization schedule is approximately the same irrespective of the type of mucin antigen.

Immunization can also be made with complete Freund's adjuvant instead of adsorption on bacteria, and the ratio between the amount of mucin and *Salmonella minnesota* can be varied. The best results have been observed when *Salmonella minnesota* is treated with acetic acid, as previously described (Young, W. W., et al., *J. Exp. Med.*, 150:1008–1019, 1979).

The host used for immunization can be a mouse or rat of any strain or any other type of animal whose splenocytes are suitable for preparation of hybridomas, i.e., susceptible to cell fusion with HAT-sensitive myeloma cell lines to establish stable hybridomas.

The immunization schedule depends upon the host animal susceptibility to mucin immunization, but the protocol described above is suitable for mice. Alternative conditions can also be applied. Suitable immunization schedules can be determined by the skilled artisan.

For example, a suitable immunization schedule for Balb/c mice is to inject the immunogen preparation intravenously through the caudal vein once a week for 5 weeks and then after a one-month intermission, boost with the immunogen preparation.

The amount of immunogen preparation administered to the host depends upon the molecular weight of the mucin, the exposure of the carbohydrate epitope, and the novelty and density of the epitope associated with mucin-type glycoproteins. The range of glycoprotein injected in mice is 3–5 µg coated on 30–50 µg of *Salmonella minnesota* suspended in 100 µl of saline, intravenously injected in each individual mouse, whose body weight range is 100–150 g.

When complete Freund's adjuvant is used, about 20 µg of glycoprotein in 500 µl of saline is emulsified with 500 µl of complete Freund's adjuvant, and about 200 µl is injected subcutaneously at multiple sites (about 50 µl per site).

Similar quantities of antigen, either coated on *Salmonella minnesota* or mixed with complete Freund's adjuvant, are used for other hosts such as rats, hamsters, or guinea pigs, and several times greater quantities are used for other hosts such as rabbits. It is not necessary to proportionately increase the amount of antigen to the body weight of the animal.

Immunization is repeated until sufficient antibody is detectable in whole serum. The spleen cells of the host are removed and splenocytes are fused with HAT-sensitive myeloma cells by the technique that has been well established (Köhler, G. and Milstein, C., *Nature*, 256:495–497, 1975 and Young, W. W. et al, supra)

HAT-sensitive myeloma cells can be NS-1, SP-1 or SP-2, for example, but any type of HAT-sensitive myeloma cells can be used. Occasionally, hybridomas can be established after fusion of host splenocytes with myeloma cells even though no antibody was detectable in the host serum. Therefore, it is not essential to detect antibodies before cell fusion. Fusions are usually carried out in polyethylene glycol, as detailed by Young et al. (supra).

A preferred myeloma cell line for use in the present invention is SP-2.

The fused cells are cultured in 96-well plates until miniclones are formed. It is important to use splenocytes 48–72 hours after the last booster injection and to fuse with well proliferating myeloma cells to obtain a number of surviving fused cells to grow. Moisture and $CO_2$ concentration in the incubator must be carefully controlled at the initial stage of culturing the fused cells.

Feeder cells are not necessary to grow the fused cells according to the process of the present invention.

One skilled in the art can readily determine suitable culture conditions.

After an appropriate culture period, hybridomas secreting antibodies that react with the glycoprotein core structure that was used to immunize are cloned and subcloned by limiting dilution, i.e., by diluting to a point where less than one cell per new culture will be expected and then plating into the wells.

In general, each well of a 96-well plate is coated with mucin glycoprotein containing the core structure used as immunogen by incubation of each well with glycoprotein solution in PBS, i.e., 5–10 µg/50 µl/well is added and incubated overnight. Glycoprotein solution is removed, washed, and futher incubated with bovine serum albumin (10 µg/50 µl/well) to block the plate before using to screen antibodies. This method is described by Hirohashi et al. (supra).

The hybridomas that secrete the antibodies that react with the particular antigens are screened as follows. Antibody bound to an antigen-coated well is usually detected by secondary antibody (anti-mouse IgM and IgG goat or rabbit antibodies) followed by $^{125}$I-labeled protein A as initially described by Young et al. (supra). The method is still more sensitive than available ELISA assays, although an ELISA can also be used. ELISA's can be more conveniently processed by use of automated readers and ELISA kits available commercially.

Monoclonal antibodies secreted by hybridomas thus isolated according to the method of the present invention can be produced in quantity by growing large batches of hybridoma cell cultures and purifying the antibody from the supernatant or by injecting mice with the hybridoma line to stimulate the production of ascites fluid. Both methods are well known in the art.

Methods of producing the monoclonal antibody in quantity according to the present invention are described in Young et al (supra).

The hybridomas isolated according to the present invention can be grown in large batches in suspension culture, or more conveniently in a fiberglass container in which cells are packed and grown in high density, wherein antibodies can diffuse into the culture medium.

The monoclonal antibodies can be purified by known methods, for example, by affinity separation using protein A or high pressure liquid chromatography on reverse phase alkylated silica gel or with a synthetic polystyrene gel filtration column.

According to the above-described method, hybridomas that secrete monoclonal antibodies can be produced which are at least qualitatively as good as those produced by conventional methods or which are even better than known monoclonal antibodies specific to human cancer-associated antigens in that the monoclonal antibodies of the prsent invention do not exhibit undesirable cross-reactivity with normal glycoproteins having a normal sugar sequence with complete glycosylated structure.

Three preferred monoclonal antibodies that have been isolated according to the method of the present inventon are BM-8, BM-3 and BM-4. The hybridomas secreting these monoclonal antibodies, designated hybridoma BM-8, BM-3 and BM-4, have been deposited with the American Type Culture Collection, Rockville, Md., and have ATCC Deposit Nos. HB-9873, HB-9653 and HB-9654, respectively.

Monoclonal antibody BM-8 according to the present invention is secreted by hybridoma BM-8 and has the following identifying characteristics:

(1) $IgG_{2a}$ isotype, (2) Reacts with Tn antigen, (3) Specific to GalNAc but not to GlcNAc, Gal or Glc, (4) Epitopic specificity to α-GalNAc and not β-GalNAc, and (5) Does not cross-react with blood group A.

Further, monoclonal antibody BM-8 binds to various cell lines as shown in FIG. 3 and described in Example 1 below. Monoclonal antibody BM-8 does not react with normal human fibroblasts BRASCH and WI-38 or with tumor cell lines HEL-299 and IMR-90.

Monoclonal antibody BM-8 also displays activation of cytotoxic cells directed to various tumor cells as shown in FIG. 4 and described in Example 1 below. Specifically, human erythroleukemia cell line K 562 and human squamous cell lung carcinoma LU-65 show a remarkable susceptibility to the antibody-dependent cytotoxicity induced by monoclonal antibody BM-8 and human fibroblasts BRASCH and WI-38 and human erythroleukemia cell line HEL 299 have no susceptibility to BM-8 dependent cytotoxicity.

Two hybridomas, NCC-LU-35 and -81, secreting IgM monoclonal antibody directed to Tn antigen have previously been established. These antibodies were obtained after immunization with lung squamous cell carcinoma LU-65 (Hirohashi et al., *Proc. Natl. Acad. Sci. USA* 82:7029–7043, 1985). The cell growth inhibitory and cytotoxic properties of BM-8 clearly distinguish this antibody from NCC-LU-35 and -81.

Monoclonal antibody BM-3 according to the present invention is secreted by hybridoma BM-3 and has the following identifying characteristics:

(1) IgM isotype, (2) Reacts with sialyl-Tn antigen and not with T antigen, and (3) Epitopic specificity to NeuAcα2→6GalNAcα1→O-ser/thr and not to NeuAcα2→6GalNAcβ1→O-ser/thr.

Monoclonal antibody BM-4 according to the present invention is secreted by hybridoma BM-4 and has the following identifying characteristics:

(1) $IgG_1$ isotype, (2) Reacts with sialyl-Tn antigen and not with T or Tn antigen, (3) Epitopic specificity to NeuAcα2→6GalNAcα1→O-Ser/Thr and not NeuAcα2→6GalNAcβ1→O-Ser/Thr, and (4) Can readily be converted to Fab or (Fab)$_2$ fragments.

Determination of Antibody Isotypes

The isotype of the monoclonal antibodies isolated according to the methods of the present invention can be determined by conventional methods such as by solid-phase radioimmunoassay using antibodies directed to isotype-specific anti-mouse antibodies, which are commercially available from various vendors, such as Cappel Laboratories.

Determination of Antibody Specificity

Specificity of antibodies isolated according to the present invention can be determined in numerous ways, including by: (1) competitive binding assays, (2) inhibition assays, and (3) binding assays to natural and enzymatically or chemically treated mucin-type glycoproteins.

Competitive Binding Assay

This assay is a solid-phase radioimmunoassay (RIA) competition assay. The assay involves using the monoclonal antibody isolated according to a method of the present invention and one or more other monoclonal antibodies known to have specificity to the same antigen that the monoclonal antibody isolated according to a method of the present invention is suspected of having. Further, the two monoclonal antibodies must have different isotypes or be from different species such that they can be separately recognized by secondary antibodies when present together.

In this assay, two incubations are performed for each monoclonal antibody having known specificity. Specifically, one incubation is conducted using one of the two monoclonal antibodies in a constant amount and using increasing amounts of the challenging monoclonal antibody. In the other incubation, the roles of the two monoclonal antibodies are reversed. That is, the one used in a constant amount in the first incubation is used in increasing amounts in the second incubation and the one used in increasing amounts in the first incubation is used in a constant amount in the second incubation.

For each incubation, the two antibodies are first mixed together and then the mixture of antibodies is incubated with the antigen of interest. Briefly, serial dilutions (about 12 dilutions are sufficient) of one antibody (about 1.5 µg to 60 nanograms) are added to about 1.5 µg of the other antibody in 100 µl of a suitable buffer, for example, PBS. The converse is then done by reversing the roles of the two monoclonal antibodies. The volume of each mixture is then adjusted to about 200 µl with the same buffer, for example, PBS, and aliquots of about 100 µl of the mixture of the two antibodies are incubated overnight at 4° C. in assay plates previously coated with the antigen of interest (about 5 µg/well) and blocked with 1% of BSA in PBS.

After incubation, the plates are washed a suitable number of times, e.g. three times, with a suitable buffer, e.g. PBS, and the amount of monoclonal antibody still bound to the antigen after the challenge is determined by reacting with a species or subclass specific antibody (e.g., an anti-mouse IgM for a mouse IgM or an anti-mouse $IgG_3$ for a mouse $IgG_3$), followed by reaction with an appropriately labeled probe.

A suitable reaction time for reacting with a species or subclass specific antibody is about 2 hours and a suitable reaction temperature is room temperature, i.e., 22°–25° C.

After the reaction, the plates are washed a suitable number of times, e.g., three times, with a suitable buffer, e.g. PBS, and an appropriately labeled probe is added. One example of a suitable probe is $^{125}$I-labeled protein A. After suitable incubation, e.g., 1.3 hours at room temperature, i.e., 22°–25° C., the plates are again washed, e.g. 5 times, with a suitable buffer, e.g., PBS, and the amount of probe is quantitated according to the type of label used. For example, an $^{125}$I-labeled probe is counted in a gamma counter.

If the binding of the monoclonal antibody isolated according to the method of the present invention to the particular antigen is competitively inhibited by the monoclonal antibody having known specificity, the monoclonal antibody isolated according to the method of the present invention can be considered to have specificity to the particular antigen.

One skilled in the art will readily recognize that this assay can also be performed omitting the second antibody, which is usually anti-mouse IgG+IgM.

Inhibition Assays

Since the antibodies isolated according to the method of the present invention are directed to glycoprotein core structures, the specificity can be determined by assaying the ability of various monosaccharides and disaccharides to inhibit the ability of the monoclonal antibody to bind to the antigen to which the monoclonal antibody is presumptively directed.

The assays are conducted by incubating the monoclonal antibody with various mono- or disaccharides. A suitable molar ratio of monoclonal antibody to saccharide ranges from about 1:5 to about 1:100 and a suitable buffer is PBS. The incubation is carried out at a temperature and for a time sufficient for the monoclonal antibody to react with the saccharides, e.g. about room temperature for 1 hour. After the incubation, aliquots of the monoclonal antibody/saccharide mixtures are removed and incubated with the antigen to which the monoclonal antibody is presumptively directed in a manner similar to that described above. That is, aliquots of the mixture are added to wells previously coated with the antigen and blocked with BSA in a suitable buffer such as PBS. Suitable incubation conditions with the antigen are overnight at 4° C.

The inhibitory effect of the different saccharides on the binding of the monoclonal antibody to the antigen is then determined by solid phase RIA as described above.

One skilled in the art can readily determine suitable saccharides to be used in the inhibition experiments.

For example, for monoclonal antibodies presumptively directed to the Tn antigen, the monosaccharides GalNAc, GlcNAc, Gal and Glc can be used. If the monoclonal antibody is indeed specific to the Tn antigen, the binding of the monoclonal antibody to the antigen should be inhibited by GalNAc but not by the other three monosaccharides.

Further, for monoclonal antibodies specific to the Tn antigen, the actual epitope of GalNAc to which the antibody is directed can be determined by conducting an inhibition assay using p-nitrophenyl α-D-GalNAc, p-nitrophenyl β-D-GalNAc, and a mixture of the α- and the mixture of β-p-nitrophenyl derivatives.

If the monoclonal antibody is specific to the Tn antigen, binding of the monoclonal antibody to the Tn antigen will be inhibited by the α-p-nitrophenyl derivative but not by the β-p-nitrophenyl derivative. Further, some inhibition, but not total inhibition will be observed with the mixture of the α- and β-p-nitrophenyl derivatives.

As a further example, if the monoclonal antibody is directed to the sialyl-Tn antigen, an inhibition assay can be carried out using monosaccharides such as GalNAc and NeuAc, L-fucose, D-galactose, D-glucose, and D-N-acetylglucosamine.

If the antibody is specific to sialyl-Tn antigen, binding of the antibody to the antigen should be inhibited by GalNAc and NeuAc, but not by the other monosaccharides.

Similarly, the disaccharide NeuAcα2→6GalNAcα1→O-serine should inhibit the reactivity of a monoclonal antibody specific to the sialyl-Tn antigen but lactose should not have inhibitory activity. However, the monoclonal antibody directed to Tn can cross-react with the NeuAcα2→6GalNAcβ1→O structure and is, therefore, inhibitable weakly by O-propyl derivatives of this structure.

Binding to Treated and Untreated Mucin-Type glycoprotein

This assay is based upon the fact that certain enzymatic and/or chemical treatment of various mucins either exposes or abolishes antigen structures. The assay is conducted as follows.

Mucin-type glycoprotein is coated on a 96-well plastic plate by incubating 10 μg/50 μl PBS/well overnight. The glycoprotein adsorbed onto the plastic surface is treated separately with each of sialidase, β-galactosidase, and α-N-acetylgalactosaminidase or left untreated. Antibody binding to such treated and untreated solid phase glycoproteins is then compared. Sialyl-Tn activity defined by antibody BM-3 can be converted to Tn activity defined by BM-8 when the sialyl-Tn antigen such as that from ovine submaxillary mucin adsorbed on a plastic surface is treated with sialidase. Glycophorin A of human erythrocytes, which has no T or Tn activity, can be converted to T or Tn antigen when adsorbed on a plastic surface and treated with sialidase (to convert it to T antigen) or successive treatment with sialidase and β-galactosidase (to convert it to Tn antigen). Such a procedure is described by Hirohashi (supra).

One skilled in the art can readily determine suitable mucin-type glycoproteins and enzymatic and chemical treatments which would be useful in the assays.

For example, if the monoclonal antibody is specific to the sialyl-Tn antigen, then a comparison of the reactivity of the antibody with OSM before and after various enzymatic degradation can be made. Specifically, approximately 90% of the carbohydrate chains on native OSM consists of sialyl-Tn antigen. However, the antigen can be destroyed by enzymatic treatment with sialidase. Thus, a monoclonal antibody which is specific to sialyl-Tn antigen would react with native OSM but not with sialidase treated OSM.

Additionally, the present inventors have found that glycophorin A in its native form does not contain T, Tn, or sialyl-Tn antigen. However, the desialylated glycophorin A exposes the T antigen but not the Tn antigen. Thus, a monoclonal antibody that binds to the T antigen should react with sialylated glycophorin A, but not with native glycophorin A.

Further, glycophorin antibody and the sialylated derivative can be used to detect monoclonal antibodies directed to the sialyl-Tn antigen. Conversion of glycophorin A to expose the sialyl-Tn antigen is difficult. If native glycophorin A is treated with influenza virus sialidase or New Castle disease virus sialidase, which cleaves sialyl 2→3Gal but not sialyl 2→6GalNAc, then the core structure would contain Galβ1→3[NeuAcα1→6]GalNAc. This structure can be further converted to the sialyl-Tn antigen by elimination of the Gal residue with β-galactosidase. However, this is practically very difficult because β-galactosidase is not efficiently eliminated when a NeuAcα2→6-linked structure is present in an adjacent position.

Until the present invention, no monoclonal antibodies directed to the T, Tn, or sialyl-Tn antigens have been intentionally produced. Rather, they are among thousands of hybridomas selected by conventional methods, i.e., based on preferential reactivity with tumor cells or tissues.

According to the present invention, such monoclonal antibodies can intentionally be produced.

Method of Preventing Growth and Replication of Cancer cells and Method of Treating Cancer The present invention also provides a method of preventing growth and replication of cancer cells and a method of treating cancer.

More specificaly, the present invention provides a method of preventing growth and replication of cancer cells that express the core structure of a mucin-type glycoprotein comprising inducing an anti-cancer cell immune response by administering to a subject a vaccine comprising:

(a) a pharmaecutically effective amount of an antigen comprising a purified mucin-type glycoprotein, a purified core structure of a mucin-type glycoprotein or a chemically synthesized carbohydrate determinant linked to a carrier molecule and which are capable of inducing an immune response against the mucin-type glycoprotein, and (b) a pharmaecutically acceptable carrier, diluent or excipient.

The antigen is one that is capable of inducing an anti-cancer cell immune response and comprises a purified mucin-type glycoprotein carrying a Tn or sialyl-Tn epitope, a purified core structure of a mucin-type glycoprotein or a chemically synthesized carbohydrate determinant linked to a carrier molecule as described above. The anti-cancer cell immune response can be production of antibodies directed against the mucin-type glycoprotein or chemically synthesized carbohydrate determinant or induction of various other types of immune responses such as induction of cytotoxic killer T-cells, anomalous killer cells (AK cells), and antibody dependent cytotoxic cells, etc.

Preferred antigens whether purified from natural sources or chemically synthesized are the T antigen, Tn antigen and sialyl-Tn antigen and the Tn-antigen and sialyl-Tn antigen are especially preferred.

Preferred antigens comprising purified mucin-type glycoproteins carrying the Tn or sialyl-Tn epitope are bovine or ovine submaxillary mucin.

Examples of anti-cancer cell antibodies which the antigens are capable of inducing in splenocytes suitable for the preparation of hybridomas are BM-8, BM-3 and BM-4 described above.

Doses and suitable pharmaceutically acceptable carriers, diluents and excipients can readily be determined by the skilled artisan.

As mentioned above, the present invention also provides a method of treating cancer wherein the cancer cells express a core structure of a mucin-type glycoprotein comprising administering to a subject a medicament comprising:

(a) a pharmaceutically effective amount of an anti-cancer antibody produced against a purified core structure of a mucin-type glycoprotein, and (b) a pharmaceutically acceptable carrier, diluent or excipient.

The antigen can be any purified core structure of a mucin-type glycoprotein such as those described above and include the T antigen, Tn antigen and sialyl-Tn antigen and the Tn antigen and sialyl-Tn antigen are particularly suitable.

The anti-cancer antibody is produced and isolated as described above.

Preferred anti-cancer antibodies include BM-8, BM-3 and BM-4.

Doses and suitable pharmaceutically acceptable carriers, diluents and excipients can readily be determined by the skilled artisan.

EXAMPLES

The invention will now be described by reference to specific examples. However, the invention is not to be construed as being limited to the examples.

Unless otherwise specified, all percents, ratios, etc. are by weight.

Example 1

Production and Characterization of Monoclonal Antibodies to Tn Antigen

Preparation of Tn Antigen

The Tn antigen was prepared from culture supernatant from human lung squamous cell carcinoma LU-65 (available from the American Type Culture Collection, Rockville, Md.) on gel filtration as described by Hirohashi et al (Hirohashi, S. et al, Proc. Nat. Acad. Sci. USA, 82:7039–7043, 1985).

Specifically, the cells were cultured in RPMI medium supplemented with 15% fetal calf serum. (However, the cells can also be cultured in other media, e.g., Dulbecco's modified Eagle's medium, and under certain conditions, cells can be cultured in chemically-defined media without supplementation of serum.)

Next, 500 ml of the supernatant obtained by centrifugation to separate cell debris was lyophilized to 1/10 of its original volume, dialyzed against distilled water, and re-lyophilized. The residue was dissolved in 10 ml of PBS; a small part of the residue was insoluble in PBS. Aliquots of 5 ml were applied to a column of Sepharose-CL4B, previously equilibrated with PBS in the presence of 0.1% sodium azide, and elution was performed with phosphate-buffered saline (PBS), i.e., 25–30 mM $NaH_2PO_4$-$Na_2HPO_4$ in 0.9% NaCl at pH 7.0. Fractions of 5.0 ml were collected, and aliquots of 100 µl from each fraction were placed in each well in 96-well plastic plates (Falcon, Microtest III, flexible assay plate, Falcon Labware, Oxnard, Calif.), and incubated at room temperature overnight in order to effect efficient adsorption of mucin-type glycoprotein on the plastic plate. Each plate was washed three times with PBS, and 150 µl of 1% BSA in PBS was added to each well. The plates were placed at room temperature (25° C.) for 2 hours in order to allow blocking of the uncovered plastic surface, i.e., in order to avoid non-specific adsorption of primary antibody to the uncovered plastic surface. Each plate was again washed three times with PBS and 100 µl of anti-Tn antibody, NCC-LU-81 (diluted 1:1000), were added to each well. The plates were placed at 4° C. for 18 hours in order to allow antigen-antibody complexes to form. The plates were again washed three times with PBS, and 50 µl of a secondary antibody (rabbit anti-mouse IgM and IgG) diluted 1:1000 with 1% BSA in PBS, was added to each well. The plates were incubated for 2 hours at 25° C. and washed three times with PBS. The secondary antibodies were purchased from Cappel Laboratories (Cochranville, Pa.). Finally, to each well was added 50 µl of $^{125}$I-labeled protein A having an approximate activity of $10^5$ cpm and the plates were incubated for 1½ hours at room temperature. The plates were washed three times with PBS and the radioactivity in each well was counted in a gamma counter to determine which fractions had Tn activity. The fractions showing the Tn activity (fractions 8–15) (Panel A, FIG. 1) were pooled and lyophilized to 1/5 of the original volume, and the sample of 1.0 ml was applied to a column of Sephacryl S-200 (1.2×110 cm). The sample was eluted with PBS, pH 7.0 and fractions of 2.0 ml were collected. Aliquots of 100 µl from each fraction were analyzed for protein concentration by UV absorption at 280 nm, and analyzed by solid-phase radioimmunoassay (RIA) for Tn activity as described above for the Sepharose-derived fractions. Only the highly active fractions at the void volume ($V_o$) were taken (see Panel B, FIG. 1), dialyzed extensively against distilled water, lyophilized, weighed, and used for immunization.

Immunization and Establishment of Monoclonal Antibodies

The high molecular weight glycoprotein Tn antigen isolated as described above was dissolved in distilled water in an amount of 4.0 mg protein/4 ml water and 16 mg acid-treated *Salmonella minnesota*, obtained by conventional methods, was added. The mixture was thoroughly mixed for 1 hour at 57° C., and then lyophilized. The lyophilized sample was then suspended in 4.0 ml of PBS and aliquots of 100 µl (i.e., 100 µl of the glycoprotein and 400 µl of bacteria) were injected intravenously through the caudal vein into each of five Balb/c mice. Injection was made once a week for five weeks and after one month of intermission, the mice were boosted with 200 µl of the antigen suspension (i.e., 200 µg of glycoprotein and 800 µg of the bacteria). Three days after the booster injection, the animals were sacrificed, the spleen cells were removed and splenocytes were fused with mouse myeloma SP-2 cells by conventional methods (Hirohashi, S. et al. *Proc. Natl. Acad. Sci. USA*, 82:7039–7043, 1985 and Fukushi, Y. et al, *J. Biol. Chem.*, 259:4681–4685, 1984).

Hybridomas secreting antibody which reacted with the Tn antigen that was used for the initial immunization and which did not react with native glycophorin A from human erythrocytes were cloned and subcloned by limiting dilution in 96-well plates (Falcon, Microtest III).

Positive reactivity with Tn antigen and negative reactivity with native glycophorin A from human erythrocytes was tested by coating µl astic plates with the Tn antigen or glycophorin A by adding 50 µl of PBS containing 5 µl of the antigen to each well and incubating at room temperature (22°–25° C.) for 18–24 hours. The antigen-coated µl ate was blocked with 1% bovine serum albumin in PBS, followed by washing with PBS. Subsequently, 50 µl of hybridoma supernatant were added and incubated for 2 hours at room temperature. Each well was then washed with PBS, followed by reaction with anti-mouse IgG+IgM and $^{125}$I-labeled protein A.

The native glycophorin A from human erythrocytes was purchased from Sigma Chemical Co., and prepared by the method described by Marchesi and Andrews (*Science*, 174:1247, 1971).

Hybridomas showing positive reactivity with Tn antigen and negative reactivity with native glycophorin A from human erythrocytes were scaled up and the reactivity of Tn antigen and glycophorin A was reexamined and, additionally, reactivity with blood group A glycolipids was examined by solid-phase radioimmunoassay as described by Hirohashi et al. (supra) and Fukushi et al (supra). The method is further described by S. Hakomori and R. Kannagi (*J. Natl. Cancer Inst.*, 71:231–257, 1983).

Seven clones showed reactivity with Tn antigen. Of these, one hybridoma which showed positive reactivity with Tn antigen and negative reactivity with glycophorin A and blood group A glycolipids was selected and recloned.

This cloned cell line was used to produce a scaled up culture in RPMI medium containing 15% fetal calf serum from which supernatants were harvested by centrifugation. The cloned cell line was also used to produce ascites fluid by conventional methods (Young et al., *J. Exp. Med.*, 150:1008, 1979)

The hybridoma and monoclonal antibody produced therefrom were designated BM-8.

Determination of Antibody Isotype

The antibody isotype was determined by solid-phase radioimmunoassay using various monoclonal antibodies directed to mouse IgM, IgG$_1$, IgG$_{2a}$, IgG$_{2b}$, and IgG$_3$ according to conventional methods. (Young et al, supra and Fukushi et al., supra).

The results showed that the isotype of antibody BM-8 is IgG$_{2a}$, the isotype of antibody BM-3 is IgM, and the isotype of antibody BM-4 is IgG$_1$.

Determination of Antibody Specificity

The specificity of BM-8 was determined by i) competitive binding of BM-8 to Tn antigen with NCC-LU-81 ("LU-81"), which is an anti-Tn antibody (Hirohashi, S. et al *Proc. Natl. Acad. Sci. USA*, 82:7039–7043, 1985); ii) inhibition of antibody binding with various monosaccharides, and iii) inhibition of antibody binding with p-nitrophenyl α- or β-D-N-acetyl-galactosaminide. Each procedure is described below.

Competitive Binding Assay: A solid-phase RIA competition assay was developed which involved incubating one monoclonal antibody in a constant amount and the challenging monoclonal antibody in increasing amounts. LU-81 and BM-8 were mixed together prior to incubation with Tn antigen as follows. In one µl ate, serial dilutions of LU-81 (1.5 µg to 60 ng) were added to 100 µl (1.5 µg) of BM-8 (12 wells); conversely, in another plate serial dilutions of BM-8 (1.5 µg to 15 ng) were added to 100 µl (1.5 µg) of LU-81 (12 wells). The volume of each well was then adjusted to 200 µl with PBS, and aliquots of 100 µl of the mixture of the two antibodies were incubated overnight in 96-well plates (Falcon, Microtest III, Felxible Assay Plate) previously coated with Tn antigen (5 µg/well) and blocked with 1% BSA in PBS, by methods analogous to those disclosed above. After incubation overnight at 4° C., the plates were washed three times with PBS. The amount of LU-81 or BM-8 still bound to Tn antigen after the challenge was determined as follows. The bound antibody was reacted for 2 hours at room temperature with subclass specific antibodies-rabbit anti-mouse IgM for the LU-81 and rabbit anti-mouse IgG$_3$ for the BM-8. After washing the plate three times with PBS, about 10$^5$ cpm (50 µl ) of $^{125}$I-labeled protein A with 1% BSA in PBS was added, and after 1.3 hours the plates were washed five times with PBS and the radioactivity remaining in the wells was counted in a gamma counter.

The results showed that the binding of BM-8 was competitively inhibited by LU-81 indicating that BM-8 is an anti-Tn antibody.

Inhibition of Antibody Binding by Monosaccharides: Initially, 200 µl of a 500 mM solution of the following monosaccharides —GalNAc, GlcNAc, Gal or Glc (Sigma Chemical Co., St. Louis, Mo.) —were double-diluted to 0.24 mM with PBS, and 100 µl of each monosaccharide solution was added to 100 µl of BM-8 and incubated at room temperature. After 1 hour, aliquots of 100 µl of the mono-clonal antibody/monosaccharide mixtures were taken and incubated overnight at 4° C. in 96-well plates (Falcon, Microtest III, Flexible Assay Plate) previously coated with Tn antigen and blocked with 1% BSA in PBS as described above. The inhibitory effect of the different monosaccharides upon the binding of BM-8 to Tn antigen was determined by solid phase RIA as described above.

The results are shown in FIG. 2A. In FIG. 2A, the closed squares represent mixtures containing GlcNAc or Glc; the closed circles represent mixtures containing GalNAc; and the open squares represent mixtures containing Gal.

The results show that binding of BM-8 antibody to Tn antigen is effectively inhibited by GalNAc, but not by GlcNAc, Glc or Gal.

These results indicate that the specificity of BM-8 is directed to GalNAc rather than GlcNAc, Gal or Glc.

Inhibition of Antibody Binding by P-nitrophenyl α-D- or β-D-GalNAc: In order to ascertain whether the GalNAc to which BM-8 binds is α- or β-GalNAc (Sigma Co.), the inhibitory activity was determined by α- and β-p-nitrophenyl derivatives as described below: p-Nitrophenyl α- or β-GalNAc was dissolved in 200 μl of dioxane/PBS, 50/50, v/v, and serially diluted from 75 mM to 0.03 mM in PBS. 100 μl of this solution was then added to 100 μl of either BM-8 or LU-81 and incubated at room temperature. After 1 hour, 100 μl of the monoclonal antibody/monosaccharide mixture was taken and incubated in plates previously coated with Tn antigen and blocked with 1%. BSA in PBS as described above, and the inhibitory effect of α- and β-p-nitrophenyl glycosides on antibody binding to Tn antigen was determined by solid phase RIA as described as above. 100 μl of Dioxane/PBS (50/50, v/v) was incubated with 100 μl of both BM-8 and LU-81 as a control for the denaturing effect of dioxane on the proteins.

The results are shown in FIGS. 2B and 2C, wherein Panel B shows the results for BM-8 and Panel C shows the results for LU-81. In Panel B, the closed circles represent mixtures containing α-GalNAc; the open triangles represent mixtures containing β-GalNAc; the open squares represent mixtures containing both α- and β-GalNAc; and the closed squares repesent mixtures containing GlcNAc. In Panel C, the open circles represent mixtures containing α-GalNAc; the open triangles represent mixtures containing β-GalNAc; the closed triangles represent mixtures containing α- and β-GalNAc; and the closed squares represent mixtures containing GlcNAc.

As can be seen from the results shown in FIG. 2B and FIG. 2C, both the BM-8 antibody of the present invention and the LU-81 antibody are inhibited from binding to the Tn antigen by p-nitrophenol-α-D-GalNAc, but not by p-nitrophenol-β-D-GalNAc. These results indicate that the epitope structure defined by antibody BM-8 is a structure exposed by the α configuration, rather than the β configuration, of GalNAc.

Reactivity of BM-8 Monoclonal Antibody with Different Cell Lines

The antibody activity of BM-8 to various cell lines was determined as described by Fukushi et al (Fukushi, Y. et al, *J. Biol. Chem.*, 259:4681–4685, 1984), and the reactivity was expressed as percent of the highest reactivity, which was displayed by human squamous cell lung carcinoma QG 56. The cell lines tested were human fibroblast BRASCH, erythroleukemia K 562, human ovarian carcinoma 78-2, lung cancer cell line LU-65 (Hirohashi, S., et al *J. Natl. Cancer Inst.*, 69:565–568, 1982), gastric cancer cell lines MKN series (Motayama, T. et al, *Acta Med. Biol.*, 27:49–63, 1979), lung cancer cell lines QG 56 and PC-9 (Oboshi, S. and Sekiguchi, M. [in Japanese] *Tampakushitsu-Kakusan-Koso (Protein-Nucleic Acid-Enzyme)*, 23:697–711, 1978), human ovarian carcinoma SKOV 3 (Fogh, J. et al, *J. Natl. Cancer Inst.*, 59:221–226, 1977), monocytic leukemia cell line THP 1 (Tsuchiya, S. et al, *Int. J. Cancer*, 26:171–176, 1980), colonic cancer cell line SW 403, human colonic cancer cell line HRT 10, human breast carcinoma cell line BT 20, human sarcoma cells transformed by SV-40 virus VA-13, human fibrosarcoma cell line HT 1080, human metastatic pancreas adenocarcinoma cell line ASPC 1, human pancreas primary adenocarcinoma cell line BXPC 3, human hepatoma cell line HUH-7, human endometrium cancer cell line ISHIKAWA, embryonic human lung cell line HEL 299, promyelogeneous leukemia cell line HL 60, human fibroblast WI-38 and human lung fetal diploid cells IMR 90 (the latter two of which were purchased from the American Type Culture Collection, Rockville, Md. 20852). Cell lines LU-65, PC-9, HL 60, K 562 and THP 1 were cultured in suspension in RPMI 1640 supplemented with 10% FCS. All other cell lines were grown in Dulbecco modified Eagle's MEM supplemented with 10% FCS. Detached cells were washed and resuspended in PBS. About $5 \times 10^4$ cells of each cell line were seeded per well in Falcon Microtest III plates, which were precoated with 0.5 mg/ml of polylysine (Sigma Chemical Co.) in PBS by incubating at room temperature (25° C.) for 18 hrs (Fukushi et al, *J. Biol. Chem.*, 259:4681, 1984; *J. Biol. Chem.* 259:10511, 1984). Plates were centrifuged for 5 minutes at 500×g, the supernatant was removed gently, and cells were fixed with 0.1% glutaraldehyde (Sigma Chemical, St. Louis, Mo.) in PBS for 1 hour at room temperature. The plates were again centrifuged for 5 minutes at 500×g and washed gently twice with PBS. The plates were then stored at −70° C. until used.

Binding of BM-8 to different cell lines was determined by solid phase RIA as folows. The plates coated with cells were blocked with 5% BSA in PBS for 2 hours at room temperature; next, 100 μl of BM-8 (2.5 μg) in PBS, pH 7.0 was placed in the wells and left for 2 hours at 4° C. The plates were then washed three times with PBS and incubated with 50 μl of the secondary antibody, rabbit anti-mouse IgG diluted 1:1000 with 1% BSA in PBS, pH 7.0, at room temperature for 2 hours. The plates were then washed three times with PBS and about $10^5$ cpm (50 μl) of IPA ($^{125}$I-labeled protein A) in PBS containing 1% BSA were added, and after 1 hour at room temperature, the plates were washed five times with PBS and the radioactivity remaining in the wells was counted in a scintillation counter.

The results of BM-8 antibody binding to various cell lines are shown in FIG. 3. Of various cell lines tested, human squamous cell carcinoma cell line QG 56 showed the highest reactivity, and human fibroblasts Bresch and WI-38 did not show any reactivity. It is important to note that the majority of human cancer cell lines showed various degrees of reactivity.

More specifically, the results clearly indiate that some cell ines (e.g., MKN 45, QG 56) showed a strong reactivity, while normal fibroblasts (e.g., BRASCH and WI-38) and some tumor cell lines (.e.g., HEL 299, IMR 90) showed no reactivity.

Purification of Monoclonal Antibody BM-8

Monoclonal antibody BM-8 was purified from ascites fluid by affinity chromatography on a silica gel-protein A column. The antibody was eluted with 3.0 M sodium thiocyanate. Fractions (1.0 ml) with activity against Tn antigen as determined by solid-phase radioimmunoassay were pooled, dialyzed against PBS, and protein was quantitated by reading $A_{280}$. The culture supernatant was concentrated to one-hundredth of its volume by ultrafiltration using Amicon concentration equipment (Amicon, Boston, Mass.). The concentrated supernatant was purified on a reverse phase C18-silica gel column, and IgM and IgG fractions were obtained.

Antibody-Dependent Cytotoxicity Assay

A 4-hour $^{51}$Cr release test was used to determine antibody-dependent cytotoxicity as described in, for example, Mischell & Shiigi, *Selected Methods in Cellular Immunolocy*, W. H. Freeman & Co., San Francisco, 1980. Peripheral blood lymphocytes from two healthy human donors were separated in Ficoll-Hypaque to provide effector cells. The ratios of effector to target cells were 100:1, 50:1, 25:1 and 12.5:1.

The target cells were cell lines K 562, LU-65, WI-38, BRASCH, MKN-45, SKOV 3, QG 56, HEL 299, HUH 7 and BXPC 3, all described above. Target cells ($10^6$) were labeled by incubating in PBS with 100 μCi of $^{51}$Cr for 1 hour at 37° C., after which the cells were washed three times and resuspended in RPMI media. The labeled target cells ($5\times10^3$) in 15 μl of media were placed in each well and varying numbers of effector cells ($5\times10^5$, $2.5\times10^5$, $1.25\times10^5$, and $6.25\times10^4$) were added per well. The mixtures were incubated for 4 hours, after which the plates were centrifuged at 500×g. The supernatants were removed and the radioactivity in 125 μl sampels was measured in a gamma counter. There were three replicates per group; spontaneous release was defined as the cpm released to medium from target cells exposed to neither antibodies nor lymphocytes, and total release was defined as the number of counts released from target cells lysed by addition of 2.0% of Triton X-100 at the end of the assay. Percent of cytotoxicity was calculated as:

experimental release–spontaneous release×100total release–spontaneous release

The antibody-dependent cytotoxicity of the various target cell lines induced by BM-8 is shown in FIG. 4. Human erythroleukemia cell line K 562 and human squamous cell lung carcinoma LU-65 are the two cell lines that showed a remarkable susceptibility to the antibody-dependent cytotoxicity induced by BM-8 antibody. In contrast, human fibroblasts BRASCH and WI-38 and human erythroleukemia HEL 299 had no susceptibility to BM-2-dependent cytotoxicity. Human squamous cell lung carcinoma QG 56 and human gastric cancer cell line MKN-45 had a relatively low susceptibility to the BM-8 antibody-dependent cytotoxicity, although these cell lines showed the strongest binding activity to the same antibody.

These results indicate that BM-8 antibody displays a clear activation of cytotoxic cells directed to some of the tumor cells. However, susceptibility of tumor cells to the antibody-dependent cytotoxicity varies greatly, and has no quantitative correlation with antigen expression.

Immunohistology of Various Tissue Sections

The immunohistological staining ability of monoclonal antibody BM-8 was determined as follows.

Both frozen and paraffin-embedded tissues were obtained from surgical operations. Tissues were embedded in OCT compound (a patented compound widely used in immunohistology, manufactured by Tissue-Tek II Division, Miles Laboratories, Naperville, Ill.), frozen in dry ice-acetone, and stored in a Revco refrigerator at −80° C. until used. Frozen sections (4–5 μm thick) were prepared using a cryostat, dried on objective glass for 30 minutes at room temperature, fixed in acetone at 4° C. for 10 minutes and washed with PBS at 4° C. Tissue sections (5–7 μm thick) were also prepared from formalin-fixed, paraffin-embedded specimens according to conventional procedures. Sections were deparaffinated in xylene for 5 minutes at 4° C., dehydrated in graded ethanol, and washed with PBS at 4° C. Both frozen sections and paraffin-embedded sections were then treated with 100% methanol contianing 0.03% hydrogen peroxide for 30 minutes at room temperature in order to block the endogenous peroxidase. After washing three times with PBS, the sections were blocked, i.e. the endogenous peroxidase was inactivated, by incubation with normal horse serum for 30 minutes at room temperature. Subsequently, sections were washed three times with PBS, incubated with primary antibody solution (BM-8 culture supernatant; antibody concentration, 50 μg/ml) overnight at 4° C. in a moist chamber. After washing three times with PBS, sections were incubated with the biotinylated second antibody, diluted 1:100 (biotinylated horse anti-mouse IgG, Vector Lab, Inc., Burlingame, Calif.) for 1 hour at room temperature in a moist chamber. After washing three times with PBS, sections were incubated with a 1:100 by volume diluted solution of preformed avidin-biotinylated peroxidase complex (Vector Lab, Inc., Burlingame, Calif.) for 1 hour at room temperature in a moist chamber. After rinsing three times with PBS and 50 mM Tris/HCl buffer (pH 7.6), the sections were incubated in 50 mM Tris/HCl buffer, pH 7.6, containing 0.05%, 3-3' diaminobenzidine (Sigma Chemical Co., St. Louis, Mo.) and 0.03% hydrogen peroxidase for 10 minutes, followed by counterstaining in hematoxylin. The sections were then dehydrated in graded ethanol, xylene and mounted.

The incidence of positive staining in various cancers and normal tissues by monoclonal antibody BM-8 is summarized in Table 1.

TABLE 1

Distribution of Tn antigen defined by antibody BM-8 in various human cancers and normal tissues.

| Tissue | | Positive | Negative | Percent |
|---|---|---|---|---|
| stomach | | 7 (1)[a] | 1 (0) | 87.5 |
| colon | C[b] | 7 (4) | 1 (1) | 87.5 |
| | N | 2 (2)[c] | 4 (4) | 33.3 |
| lung | C | 7 (4) | 3 (2) | 70.0 |
| | N | 0 | 7 (4) | 0 |
| breast | C | 13 (9) | 2 (1) | 86.7 |
| | N | 2 (1) | 4 (2) | 33.3 |
| melanoma | | 3 | 7 | 30.0 |
| ovary | | 33 | 10 | 76.7 |
| TOTAL | C | 70 (18) | 24 (4) | 74.5 |
| | N | 4 (3) | 15 (10) | 21.0 |

[a]number of frozen samples in parentheses
[b]C = cancer, N = normal tissue
[c]only goblet cells are positive The results shown in Table 1 clearly indicate that anitbody BM-8 defining Tn antigen showed a high incidence of positive staining of stomach, colonic, lung, and breast cancer. Low inncidence of positive staining of normal colon and normal breast is also shown, although the intensity of the staning was quite low.

Example 2

Production and Characterization of Monoclonal Antibodies to Sialyl-Tn Antigen

Ovine submaxillary mucin (OSM) was used as the source of the sialyl-Tn antigen. Approximately 90% of the carbohydrate chain on OSM consists of the sialyl-Tn antigen.

OSM was isolated from ovine submaxillary glands by conventional methods. (Tettamanti, G. and Pigman, W. Arch. Biochem. Biophys., 124:45–50, 1968).

Briefly, aqueous extract of submaxillary glands was precipitated at acidic pH (e.g., 3.5). This is called a mucin clot. The mucin clot was centrifuged, dissolved in water, the pH adjusted to neutral, and fractional ethanol precipitation in sodium acetate performed.

The thus isolated OSM was used as was for the immunogen composition.

Immunization and Establishment of Monoclonal Antibodies

Balb/b mice were immunized as described in Example 1.

The spleen cells were removed and splenocytes were fused with mouse myeloma SP-2 cells by conventional methods as described in Example 1.

Hybridomas which grew on selective media were screened for monoclonal antibody reactivity with the above-described OSM, desialylated OSM, bovine submaxillary mucin (BSM) (approximately 50% of the carbohydrate chains on BSM consist of sialyl-Tn antigen), and glycophorin A, by methods analogous to those described in Example 1. Bovine submaxillary mucin (BSM) and glycophorin A were purchased from Sigma Chemical Company, St. Louis, Mo.

OSM was desialylated by treatment with 0.1 unit/ml of neurominodase from *Clostridium Perfringens* Type X (Sigma) by conventional methods. (Magnani, J. L. et al., *J. Biol. Chem.*, 257:14365, 1982 and Fukushi et al., *J. Biol. Chem.*, 259:10511, 1984).

Approximately 22 hybridomas were found which secreted monoclonal antibody that gave a positive reaction with OSM.

These hybridomas were scaled up and the reactivity of the monoclonal antibodies was reexamined with OSM, desialylated OSM, BSM, and glycophorin A.

Two hybridomas secreting monoclonal antibodies showing strong reactivity with OSM, weak reactivity with BSM, and no reactivity with glycophorin A or sialidase-treated OSM were recloned and used for futher study.

The hybridomas and monoclonal antibodies produced therefrom where designated BM-3 and BM-4

Determination of Antibody Isotypes

The antibody isotypes were determined by solid-phase radioimmunoassay as described in Example 1. The results indicated that the antibody BM-3 is of the IgM isotype and that the antibody BM-4 is of the $IgG_1$ isotype.

Determination of Antibody Specificity

Specificity of BM-3 and BM-4 was determined by i) reactivity with native OSM compared to reactivity with sialyladase treated OSM; and ii) inhibition of antibody binding with various monosaccharides and disaccharides. Each procedure is described below.

Reactivity with Native and Sialidase Treated OSM

In order to determine the nature of the antigen(s) expressed by OSM, native OSM and sialidase treated OSM was reacted with anti-Tn (present in ascites fluid from the monoclonal antibody CA3239) and with anti-T present in the culture supernatant of the monoclonal antibody HH8 (Clausen, H. et al., In: *Glycoconjugates*, Proceedings of the IXth International Symposium, Lille, France, p. F49, 1987).

The determination was made by solid-phase radioimmunoassay. OSM and sialidase-treated OSM were coated on a 96-well plate by incubating at room temperature for 18 hours, blocked with 1% BSA for 2 hours, followed by washing 3× with BSA. Primary antibody (anti-Tn or anti-T HH8 antibody) was added and reacted at room temperature for 2 hours, followed by washing with PBS. The antibody bound to solid-phase OSM or sialidase-treated OSM was quantitated by secondary antibody and $^{125}$I-labeled protein A. The procedure has been described in numerous publications (Hirohashi, et al., supra, Fukushi et al, *JBC*, 259:4681, 1984; *JBC*, 259:10511, 1984; Young et al. *J. Exp. Med.*, 150:1008, 1979).

The results showed that native OSM showed a weak reactivity with anti-Tn from CA3239; however, the reactivity was greatly enhanced after sialidase treatment. Further, no reactivity was observed with anti-T from HH8 before or after treatment with sialidase.

These reactivities indicate that OSM does not express the T or Tn antigen but strongly expresses the sialyl-Tn antigen.

The specificities of monoclonal antibodies BM-3 and BM-4 were characterized by reacting with native OSM and with sialidase-treated OSM. Native OSM contains sialyl2→6GalNAcα1→O-Ser/Thr as the major carbohydrate group and BM-3 and BM-4 reacted with this thereby indicating that both BM-3 and BM-4 recognize the sialyl-Tn antigen. Further the reactivity of BM-3 and BM-4 completely disappeared on sialidase treatment of OSM, in which all sialyl-Tn groups are converted to Tn residues thereby indicating that BM-3 and BM-4 do not react with T antigen. The treatment of sialidase with OSM was made on solid-phase adsorbed on a plastic surface. The method has been previously described by Hirohashi et al. (supra).

The results for BM-3 are shown in FIG. 5 where Panel A shows the reactivity of BM-3 with OSM at various concentrations of BM-3 supernatant and Panel B shows the reactivity of BM-3 with various concentrations of OSM. The closed circles indicate reactivity with native OSM and the open circles indicate reactivity with neuriminidase (or sialidase) treated OSM.

The results show that monoclonal antibody BM-3 has reactivity with native OSM, and the reactivity is greatly reduced after sialyladase treatment.

Thus, monoclonal antibody BM-3 is specific to the sialyl-Tn antigen.

The same was found for monoclonal antibody BM-4.

Inhibition of BM-3 and BM-4 Antibody Reactivity by Mono- and Disaccharides

Monosaccharide solutions were double diluted from a starting concentration of 500 mM in a series of wells assembled on 96-well plates. To each monosaccharide solution was added BM-3 or BM-4 antibody (10–50 ng/well) and the solution was incubated for 1 hour at room temperature. A series of plastic wells on 96-well plates was precoated with OSM as previously described (incubation of OSM in saline at room temperature overnight) and prewashed with BSA. The reaction mixture of monosaccharide or oligosaccharide with antibody was transferred onto the OSM-coated plate, incubated for 2 hours, followed by washing with BSA and detection of antibody-binding by secondary antibody and $^{125}$I-labeled protein A, as previously described. The degree of inhibition was compared with the antibody without mixing with monosaccharide or disaccharide and expressed as % reactivity of control.

The results for BM-3 are shown in FIG. 6 wherein Panel A shows the inhibition of BM-3 with the monosaccharides fucose (open circles), galactose (open squares), glucose (closed triangles), N-acetylglucosamine (open triangles), N-acetylgalactosamine (closed squares), and N-acetylneuraminic acid (closed circles), and Panel B shows inhibition of BM-3 with the disaccharide NeuAcα2→6GalNAcα1→O-serine (closed squares) and lactose (closed circles).

The results show that only the monosaccharides GalNAc and NeuAc were able to inhibit the binding of BM-3 to OSM and BSM, whereas the other monosaccharides, L-fucose, D-galactose, D-glucose and D-N-acetylglucosamine, were unable to inhibit the reactivity. The inhibitory activity of NeuAc was stronger than that of a GalNac. The disaccharide NeuAcα2→6GalNAcα1→O-serine also inhibited the reactivity of BM-3, whereas its anomeric isomer, NeuAcα2→6GalNAcβ1→O-propyl, and lactose did not have any inhibitory activity.

These results indicate that the hapten structure recognized by BM-3 antibody is NeuAcα2→6GalNAcα1→O-Ser/Thr, which is precisely the sialyl-Tn structure.

The same results were obtained for BM-4.

Immunohistology of Various Tissue Sections

The immunohistological staining ability of monoclonal antibodies BM-3 and BM-4 was performed as previously described (Fukushi et al. *J. Exp. Med.*, 159:506, 1984).

Briefly, specimens were fixed in formalin and embedded in paraffin for detection of antigens. Monoclonal antibodies were applied to deparaffinized tissue sections and incubated overnight at 4° C. Detection of bound monoclonal antibodies was performed with biotinyl-anti-mouse IgG+IgM and biotinyl-peroxidase complex (vectastain ABC kit; Vector Laboratories Inc.). Enzyme activity was demonstrated by 0.05M Tris containing 0.02% deaminobenzidine tetrahydrochloride and 0.005% hydrogen peroxide. These procedures are elaborated in various hydrogen peroxide. These procedures are elaborated in various monographs, for example, "Immunoenzymatic Method" by K. Watanabe and P. K. Nakane (Interdisciplinary Publications, Toshima, Tokyo, 1985).

The typical immunohistologic picture with peroxidase staining is shown in FIGS. 7A–7D and 8A–8C.

FIGS. 7A–7D show immunoperoxidase staining of formalin-fixed paraffin-embedded malignant tumors using BM-3 monoclonal antibody. The figure shows that BM-3 monoclonal antibody reacts with a lung adenocarcinoma but not with normal lung which are not stained (Panel A). Further BM-3 monoclonal antibody reacts with moderately differentiated colon adenocarcinoma, but not with surrounding normal cells and stroma which are not stained (Panel B). BM-3 monoclonal antibody also reacts in a heterologous manner with mucinous stomach carcinoma cancer cells (Panel C) and with acinar lung adenocarcinoma but not with normal lung tissue which is not stained (Panel D).

FIGS. 8A–8C show immunoperoxidase staining of formalin-fixed paraffin-embedded malignant tumors using BM-4 monoclonal antibody. The figure shows that BM-4 monoclonal antibody reacts with a lung adenocarcinoma (Panel A), with muccinous stomach carcinoma (Panel B), and with moderately differentiated colon adenocarcinoma but not with normal colon cells or stroma (Panel C).

The incidence of positive staining in various cancers and normal tissues by monoclonal antibodies BM-3 and BM-4 as compared with other anti-sialyl Tn antibodies (B72.3, NCC-LU-35, and NCC-LU-81) is shown in Table 2 below. Since the incidence of positive staining of normal tissue by BM-3 and BM-4 is very limited, positive figures with normal tissue are omitted.

TABLE 2

Immunohistochemical reactivity of monoclonal antibodies BM-3, BM-4, B72.3, NCC-Lu-35, and NCC-Lu-81 with tissue sections from various human cancers.

| Cancer type | BM-3 | BM-4 | B72-3 | NCC-Lu-35 | NCC-Lu-81 |
| --- | --- | --- | --- | --- | --- |
| lung | 2/9 | 3/9 | 3/9 | 3/9 | 2/9 |
| liver | 9/10 | 0/10 | 0/10 | — | 0/10 |
| stomach | 7/10 | 10/10 | 10/10 | — | 10/10 |
| colon | 8/10 | 10/10 | 10/10 | — | 8/10 |
| breast | 1/2 | 2/2 | 1/2 | 1/2 | 1/2 |
| pancreas | 1/8 | 8/8 | 8/8 | 8/8 | 7/7 |

Although both BM-3 and BM-4 monoclonal antibodies are directed to sialyl Tn, the incidence of positive staining was much higher with monoclonal antibody BM-4. Both antibodies, in contrast to BM-8, showed much lower incidence of positive staining of normal tissue.

Example 3

Inhibition of Syngeneic Tumor Growth in Mice by Immunization with Mucin Glycoprotein Containing Tn Epitope Bovine submaxillary mucin (BSM) containing Tn antigen was purified by the procedures described by Hill et al. (Hill HD, et al *J Biol Chem* 252:3791–3798, 1977). Bovine submaxillary glands were homogenized in 0.01M NaCl. The supernatant was adjusted to pH 4.7, and the precipitate was removed. The supernatant was applied to a sulphopropyl-Sephadex C-25 column, and the fractions containing Tn and sialyl-Tn antigens detected by monoclonal antibodies were combined. Mucin was precipitated by addition of acetyltrimethylammonium bromide and centrifuged. The precipitate was redissolved in 4.5M $CaCl_2$ and absolute ethanol to a concentration of 60%. The precipitate was discarded, and the supernatant was brought to 75% ethanol. Mucin was collected by centrifugation at 27,000 g for 30 min. The precipitate was dispersed in 1M NaCl and dialyzed against 10 mM sodium phosphate, pH 6.8. The mucin was applied to an hydroxylapatite column, and fractions containing Tn and sialyl-Tn activity were collected. Mucin was treated with neuraminidase (N-BSM) (from *Clostridium perfringens*) and applied to a Sepharose CL-4B column. Fractions containing Tn activity were pooled, dialyzed, and lyophilized.

Female CAF1 mice were immunized intraperitoneally (I.P.) with either PBS, Freund's adjuvant (FA), or N-BSM (20 µg) emulsified with complete FA. One week later mice were reimmunized I.P. with PBS, incomplete FA or N-BSM (40 µg) emulsified with incomplete FA. Ten days after the second immunization, mice were challenged with syngenic mammary tumor TA3HA cells ($10^4$ cells, injected subcutaneously). Tumor size, survival of mice, and antibody production were monitored in the mice and the results are shown in FIG. 9 and FIG. 11.

In FIG. 9 the solid line represents the group immunized with FA alone and the dashed line repesents mice immunized with N-BSM. FIG. 9 shows that all the mice in the control FA group died 14 days after the tumor challenge, whereas 3/7 mice in the group immunized with BSM survived 19 days after the challenge.

As shown in FIG. 10, the BSM-immunized group had a high titer of antibodies in sera specific to Tn and sialyl-Tn, whereas no antibodies to T epitope (neuraminidase-treated glycophorin A) were detected. In FIG. 10, open squares represent antibody titers against N-BSM (Tn); open triangles represent antibody titers against ovine submaxillary mucin (OSM) (sialyl-Tn), closed squares represent antibody titers against neuraminidase-treated glycophorin A (T). No antibody titers to Tn antigen were detected in the PBS- or FA-immunized animals.

FIG. 11 shows the effect of N-BSM immunization on tumor size. Open squares indicate the mice immunized with FA; plus signs indicate the mice immunized with N-BSM in Freund's adjuvant. Although the tumor grew in both PBS- and BSM-immunized mice, the rate of tumor growth was retarded in the BSM-immunized group as compared with the PBS-immunized group.

Example 4

Chemical Synthesis of Tn and Sialyl-Tn Antigens Conjugated with Carrier Macromolecules The basic idea for the preparation of multivalent antigen systems is summarized in FIG. 12A, Scheme I, in which the use of lysyllysine as a core matrix bearing multiple antigens as dendritic arms constitutes an essential part of the proposal. Sequential conjugation with lysyllysine, in which three amino acid groups are available as reactive ends, will generate $3^n$ Tn antigen residues. These residues will be subsequently converted to sialyl-Tn (NeuAcα2→6GalNAcα1→R) by chemical or enzymatic sialylation. In order to avoid the multiple steps of chemical reaction involved in chemical sialylation, enzymatic sialylation using CMP-NeuAc (cytidine-monophospho-sialic acid) and 2→6sialyltransferase would be preferable. These conjugates will be used as the immunizing antigens after conjugation to a carrier protein. Synthesis of a multiple-antigen peptide system (MAP) using t-butoxycarbonyl (Boc) β-Ala-O-CH$_2$-Pan resine and lysine core was previously described (Tam J P, *Proc. Natl. Acad. Sci. USA* 85:5409–5413, 1988).

Synthesis of trivalent conjugates is accomplished by the coupling of the N-hydroxysuccinimyl derivative of Tn antigen with lysyllysine. The complete reaction sequence is shown in FIG. 11, Scheme 12B. The antigen 1 is synthesized according to published procedures (Paulsen H and Holek J-P, *Carbohydr. Res.* 109:89–107, 1982; Grundler G and Schmidt R R, *Liebigs Ann. Chem.* 1826–1847, 1984). To eliminate the cationic nature of an amino group, which gives rise to highly charged conjugates, the amino group of serine needs to be modified by selective N-acetylation with acetic anhydride in methanol. The resulting compound 2 is converted to its N-hydroxysuccinimide derivative in the presence of dicyclohexylcarbodiimide as a condensation agent. The coupling reaction of 3 with 4 (Bachem Bioscience Inc., Philadelphia, Pa.) is achieved by using a 4.5M excess of 3, yielding trivalent conjugate 5. After purification by P2 column chromatography with H$_2$O, conjugate 5 is converted to its active ester 6 for further coupling with 4 or with a carrier protein.

While the invention has been described in detail and with reference to specific embodiments thereof, it will be apparent to one skilled in the art that various changes and modifications can be made therein without departing from the spirit and scope thereof.

STATEMENT OF DEPOSIT

The hybridoma cell lines BM-8, BM-3 and BM-4 were deposited with the American Type Culture Collection, 12301 Parklawn Drive Rockville, Md. 20852 on Oct. 21, 1988, Mar. 2, 1988 and Mar. 2, 1988, respectively, and have Deposit Nos. HB-9873, HB-9653 and HB-9654, respectively.

The deposits were made in accordance with the terms of the Budapest Treaty on the International Recognition of the Deposit of Microorganisms for the purposes of Patent Procedure.

All restrictions to access will be irrevocably removed upon grant of a United States patent on the instant application.

What is claimed is:

1. A method of reducing the growth rate of a cancer cell comprising a Tn or sialyl Tn epitope comprising:
   (1) immunizing a subject with a composition consisting essentially of:
      (a) an effective amount of an isolated agent comprising a Tn or sialyl Tn epitope; and
      (b) a pharmaceutically acceptable carrier, diluent or excipient; and
   (2) administering an adjuvant to said subject.

2. The method of claim 1, wherein said adjuvant is said pharmaceutically acceptable carrier, excipient or diluent.

3. The method of claim 2, wherein said agent is chemically synthesized.

4. The method of claim 1, wherein said agent is a carrier macromolecule.

5. The method of claim 1, wherein said agent is a purified mucin-type glycoprotein comprising a Tn or sialyl-Tn epitope.

6. The method of claim 5 wherein the purified mucin-type glycoprotein comprising a Tn or sialyl-Tn epitope is bovine submaxillary mucin or ovine submaxillary mucin.

7. The method of claim 1, wherein said agent is a purified core structure of a mucin-type glycoprotein comprising a Tn or sialyl-Tn epitope.

8. The method of claim 1, wherein said agent is a chemically synthesized carbohydrate component comprising a Tn or sialyl-Tn epitope.

9. The method of claims 1, 2, 3, 4, 5, 6, 7 or 8, wherein the subject is human.

* * * * *